US012779171B2

(12) United States Patent
Yoshimoto et al.

(10) Patent No.: US 12,779,171 B2
(45) Date of Patent: Nov. 3, 2026

(54) MEDICAL ELONGATED BODY

(71) Applicant: TERUMO KABUSHIKI KAISHA, Tokyo (JP)

(72) Inventors: Shosei Yoshimoto, Odawara (JP); Ryo Okamura, Fujinomiya (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 764 days.

(21) Appl. No.: 18/175,162

(22) Filed: Feb. 27, 2023

(65) Prior Publication Data

US 2023/0218860 A1 Jul. 13, 2023

Related U.S. Application Data

(63) Continuation of application No. PCT/JP2021/031665, filed on Aug. 30, 2021.

(30) Foreign Application Priority Data

Aug. 31, 2020 (JP) ................................ 2020-145818

(51) Int. Cl.
*A61B 17/34* (2006.01)
*A61M 25/00* (2006.01)
*A61M 25/06* (2006.01)

(52) U.S. Cl.
CPC ..... *A61M 25/0097* (2013.01); *A61B 17/3415* (2013.01); *A61B 17/3417* (2013.01); *A61M 2025/0057* (2013.01); *A61M 25/0662* (2013.01)

(58) Field of Classification Search
CPC .......... A61M 25/0097; A61M 25/0111; A61M 25/0662; A61M 2025/0056–0057;
(Continued)

(56) References Cited

U.S. PATENT DOCUMENTS 5,290,310 A * 3/1994 Makower ........... A61B 17/0057 128/DIG. 8
5,797,886 A * 8/1998 Roth .................. A61J 15/0092 604/264

(Continued)

FOREIGN PATENT DOCUMENTS

JP H10295699 A 11/1998
JP 2018033792 A 3/2018

(Continued)

OTHER PUBLICATIONS

International Search Report (PCT/ISA/210) with translation and Written Opinion (PCT/ISA/237) mailed on Oct. 19, 2021, by the Japan Patent Office as the International Searching Authority for International Application No. PCT/JP2021/031665. (9 pages).

(Continued)

*Primary Examiner* — Nathan R Price
(74) *Attorney, Agent, or Firm* — BUCHANAN INGERSOLL & ROONEY PC

(57) ABSTRACT

An introducer sheath, which is a medical elongated body, includes: a catheter main body; a hub fixed to a proximal portion of the catheter main body; a drug portion disposed on an outer surface of the catheter main body; and a support member configured to be connected to the hub and cover the drug portion of the catheter main body, in which the support member has a base portion rotatable in a circumferential direction of the catheter main body and a covering member disposed so as to protrude from a distal end of the base portion and cover the drug portion while overlapping at least a part of the base portion in a radial direction of the catheter main body, and the covering member is configured to move relative to the catheter main body and expose the drug portion as the base portion rotates.

20 Claims, 19 Drawing Sheets

(58) Field of Classification Search
CPC .. A61M 2025/0098; A61M 2025/0681; A61B 17/3415; A61B 17/3494–3496; A61B 2017/3482–349
See application file for complete search history.

(56) References Cited

U.S. PATENT DOCUMENTS

| | | | | | |
|---|---|---|---|---|---|
| 10,625,048 | B2 * | 4/2020 | Wada | A61M 25/0045 | |
| 11,511,083 | B2 * | 11/2022 | Wada | A61M 25/0662 | |
| 2016/0375222 | A1 * | 12/2016 | Wada | A61M 25/0054 | 604/524 |
| 2018/0056036 | A1 | 3/2018 | Wada | | |
| 2019/0192826 | A1 | 6/2019 | Wada | | |
| 2022/0379077 | A1 * | 12/2022 | Okamura | A61M 25/0043 | |
| 2023/0218877 | A1 * | 7/2023 | Yoshimoto | A61M 39/0247 | 604/510 |

FOREIGN PATENT DOCUMENTS

| | | | |
|---|---|---|---|
| WO | 2014123381 | A1 | 8/2014 |
| WO | 2018043427 | A1 | 3/2018 |

OTHER PUBLICATIONS

English Translations of the International Search Report (Form PCT/ISA/210) and the Written Opinion of the International Searching Authority (Form PCT/ISA/237) issued Oct. 19, 2021, by the Japan Patent Office in corresponding International Application No. PCT/JP2021/031665. (5 pages).

* cited by examiner

MEDICAL ELONGATED BODY

CROSS-REFERENCES TO RELATED APPLICATIONS

This application is a continuation of International Patent Application No. PCT/JP2021/031665 filed on Aug. 30, 2021, which claims priority to Japanese Patent Application No. 2020-145818 filed on Aug. 31, 2020, the entire content of both of which is incorporated herein by reference.

TECHNOLOGICAL FIELD

The present invention generally relates to a medical elongated body.

BACKGROUND DISCUSSION

In the medical field, procedures are performed to percutaneously insert, for example, various catheters into living bodies. In such a procedure, an introducer sheath or the like is used as a medical instrument connecting the inside of a living body and the outside of the living body so that various catheters or the like are percutaneously inserted into the living body. For example, the introducer sheath includes a catheter main body percutaneously inserted into a living body lumen such as a blood vessel and a hub connected to the proximal side of the catheter main body.

In a procedure in which the introducer sheath is used, an operator percutaneously inserts the catheter main body of the introducer sheath into the blood vessel via a puncture site (perforation) formed in, for example, a patient's limb with a dilator inserted in the introducer sheath. The operator removes the dilator from the introducer sheath with the distal side of the catheter main body inserted in the blood vessel. As a result, the introducer sheath forms an access route interconnecting the inside of the living body and the outside of the living body with the catheter main body percutaneously inserted in the living body lumen. After removing the dilator from the introducer sheath, the operator can insert a guide wire, various catheters, or the like into the blood vessel via the lumen of the catheter main body.

The operator inserts a guide wire or various catheters into the blood vessel, treats the lesion site in the blood vessel, and then removes the introducer sheath from the inside of the blood vessel and performs hemostasis at the introducer sheath-inserted puncture site. Typically, in performing the puncture site hemostasis, the operator puts pressure on the puncture site with, for example, a hemostatic instrument putting pressure on a puncture site.

However, the puncture site hemostasis requires pressure on the puncture site for a long time. In addition, the operator needs to operate the hemostatic instrument such that, for example, no arterial occlusion occurs despite hemostatic work for a long time by decreasing over time the pressure force with which the hemostatic instrument or the like puts pressure on the puncture site. Accordingly, a technique with which bleeding can be stopped in a short time is required in order to reduce a patient's physical burden related to puncture site hemostasis and simplify an operator's hemostasis work.

In recent years, as described in International Patent Application Publication No. 2018/043427, a method has been proposed by which puncture site hemostasis is promoted by a hemostatic agent that enables wound healing, and this hemostatic agent is disposed on the outer surface of the catheter main body of an introducer sheath so that the puncture site hemostasis for a patient is expedited and the patient's physical burden is reduced.

As for the introducer sheath described in International Patent Application Publication No. 2018/043427, a hemostatic agent is disposed on the outer surface of a catheter main body. In addition, as for the introducer sheath described in International Patent Application Publication No. 2018/043427, the hemostatic agent is covered with a cover member or a strain relief in order to prevent the hemostatic agent from peeling off the catheter main body before the hemostatic agent is introduced into a puncture site and prevent the hemostatic agent from being lost due to scratching or the like attributable to contact between, for example, an operator's finger or the surrounding object and the hemostatic agent.

However, as for the introducer sheath of International Patent Application Publication No. 2018/043427, when the hemostatic agent is introduced into a puncture site, it is necessary to remove the cover member or the strain relief covering the hemostatic agent to expose the hemostatic agent on the surface of the catheter main body. In addition, after the exposure on the surface of the catheter main body, it is necessary to further push the catheter main body into the blood vessel such that the hemostatic agent is disposed at the puncture site. Accordingly, in disposing a hemostatic agent at a puncture site using the introducer sheath of International Patent Application Publication No. 2018/043427, an operator needs to carefully move the catheter main body so as not to come into contact with the hemostatic agent after removing the cover member or the strain relief so as not to come into contact with the hemostatic agent. Accordingly, considering an operator's operability, the introducer sheath disclosed in International Patent Application Publication No. 2018/043427 has room for improvement in the structure at the time of hemostatic agent exposure.

SUMMARY

Disclosed here is a medical elongated body with which a drug can be exposed on the outer surface of a catheter main body by a simple operation, hemostasis can be expedited at a patient's puncture site, and the patient's burden and an operator's burden can be reduced.

A medical elongated body according to one aspect includes: a catheter main body; a hub fixed to a proximal portion of the catheter main body; a drug portion disposed on an outer surface of the catheter main body; and a support member configured to be connected to the hub and cover the drug portion of the catheter main body, in which the support member has a base portion rotatable in a circumferential direction of the catheter main body and a covering member disposed so as to protrude from a distal end of the base portion and cover the drug portion while overlapping at least a part of the base portion in a radial direction of the catheter main body, and the covering member is configured to move relative to the catheter main body and expose the drug portion as the base portion rotates.

According to at least one embodiment, a drug can be exposed on the outer surface of the catheter main body by a simple operation, hemostasis can be expedited at a patient's puncture site, and the patient's burden and an operator's burden can be reduced. In other words, with the medical elongated body, it is possible to expose the drug portion covered with the covering member in a living body tissue by the simple operation of percutaneously inserting the catheter main body into a blood vessel from a puncture site and rotating the base portion in a predetermined direction with the covering member inserted in the puncture site. In addition, in the medical elongated body, the operation for exposing the drug portion is only the rotation of the base portion, and thus the drug portion can be quickly exposed in the living body tissue. Accordingly, an operator can place a drug at the puncture site by a simple operation, and the time of hemostasis of the puncture site can be shortened by the hemostatic action of the drug. In particular, in the case of using in combination with a hemostatic instrument for pressure hemostasis at a puncture site, since the hemostasis time can be shortened by the drug, it is possible to reduce the risk of arterial occlusion or the like while reducing the operator's labor such as a decompression operation. Further, in the medical elongated body, when the drug portion is exposed, the catheter main body does not move from the state of being placed at the puncture site, and thus there is no adverse effect such as twisting on the puncture site or its surroundings. In addition, since the drug portion is covered with the covering member in a state where the base portion is yet to be rotated, contact with the living body tissue or another member can be prevented.

According to another aspect, a medical elongated body comprises: a catheter main body possessing a distal end and proximal portion terminating at a proximal end, with the catheter main body including a lumen that is open at opposite ends and that extends in an axial direction of the catheter main body from the distal end of the catheter main body to the proximal end of the catheter main body; a hub fixed to the proximal portion of the catheter main body; a drug that contains a hemostatic agent to treat a wound site in a living body, the drug being located on an axially extending drug covered region on the outer surface of the catheter main body; a base that is tubular and includes a proximal end and a distal end, with the base being rotatably connected to the hub and being rotatable relative to the catheter main body; and a cover that includes a distal portion extending distally beyond the distal end of the base, with the cover extending axially over a longitudinal extent that axially overlaps with at least a distal portion of the drug covered region on the outer surface of the catheter main body at which the drug is located so that the distal portion of the drug covered region on the outer surface of the catheter main body at which the drug is located is covered by the distal portion of the cover. The cover includes a proximal portion operatively connected to the base so that the rotation of the base results in movement of the distal portion of the cover that uncovers and exposes the drug in the distal portion of the drug covered region.

In accordance with another aspect, a method comprises inserting a catheter main body into a blood vessel in a patient's body via a puncture site in the patient's body, wherein the catheter main body possesses an outer surface and also possesses a proximal portion at which is fixed a hub, and a base rotatably mounted on the hub. The inserting of the catheter main body into the blood vessel includes inserting the catheter main body into the blood vessel so that a drug on the outer surface of the catheter main body is covered by a cover so that the drug is not in contact with living body tissue of the patient's body. The method additionally involves exposing the drug after the inserting of the catheter main body into the blood vessel so that the drug contacts the living body tissue, where the exposing of the drug includes moving the cover so that the drug is exposed to the living tissue, and the moving of the cover being accomplished by rotating the base relative to the catheter main body.

DETAILED DESCRIPTION

Figure 1:
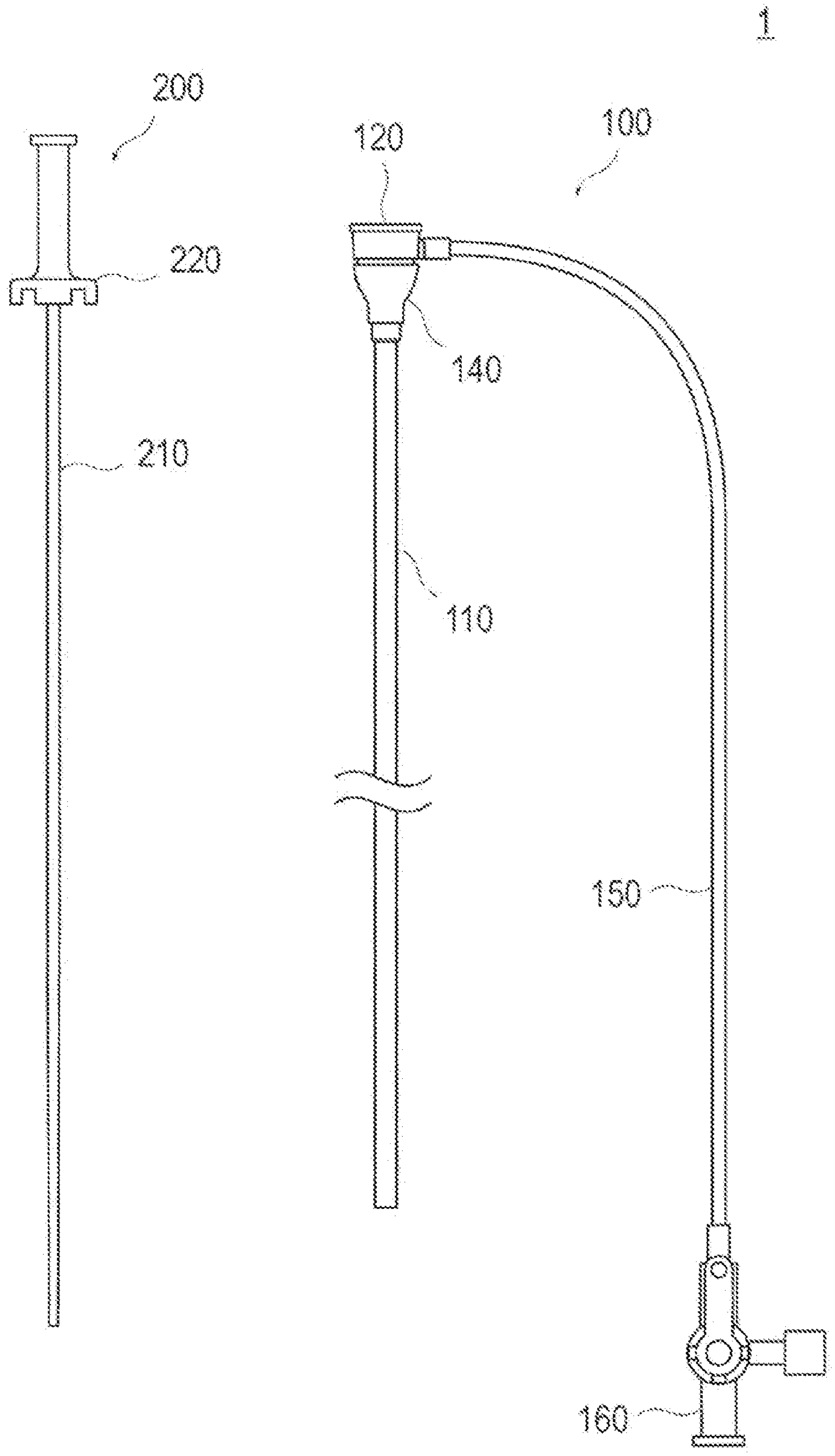
FIG. 1 is a plan view illustrating the configuration of an introducer assembly including an introducer sheath representing an example of a medical elongated body according to a first embodiment.

Set forth below with reference to the accompanying drawings is a detailed description of embodiments of a medical elongated body and method representing examples of the new medical elongated body and method disclosed here. The embodiments illustrated and described here are exemplifications for embodying the technical idea(s) disclosed here and do not limit the invention. In addition, other possible forms, examples, operation techniques, and so on conceivable by those skilled in the art or the like without departing from the spirit of the disclosure here are included in the scope and spirit of the invention and are included in the scope of the invention described in the claims and the equivalent thereto.

Further, although the accompanying drawings may be schematically represented with the scale, aspect ratio, shape, and so on appropriately changed from the actual object for convenience of illustration and comprehension, the drawings are merely examples and do not limit the interpretation of the invention.

It should be noted that, as for the operation direction of each portion configuring the medical elongated body in the present specification, for example, the side of insertion into a living body lumen in the direction along the axial direction of a catheter main body 110 will be referred to as "distal side" (or distal portion), and the side that is positioned on the side opposite to the distal side in the axial direction and where an operator operates at hand (side where the catheter main body 110 is removed) will be referred to as "proximal side" (or proximal portion). In addition, the direction parallel to the axial direction of the catheter main body 110 of the medical elongated body will be referred to as "forward-backward direction", and the direction along the circumferential direction of the catheter main body 110 (direction around the axial direction of the catheter main body 110) will be referred to as "rotation direction". The "distal end" terminology means a certain range in the axial direction including the most distal end, and the "proximal end" terminology means a certain range in the axial direction including the most proximal end.

In addition, although ordinal numbers such as "first" and "second" are added in the following description, unless otherwise specified, the numbers are for convenience and do not specify any order.

The medical elongated body according to one embodiment is an example applied to introducer sheaths 100, 300, and 400 forming part of an introducer assembly 1, but the application or use of the medical elongated body is not particularly limited. In addition, the content of a specific procedure, a treatment procedure, and so on using the medical elongated body according to one embodiment are also just examples and do not limit the invention.

First Embodiment

First, the medical elongated body according to a first embodiment will be described with reference to FIGS. 1 to 6 as appropriate. In the first embodiment, the medical elongated body is an example applied to the introducer sheath 100 forming part of the introducer assembly 1.

As illustrated in FIG. 1, the introducer assembly 1 has the introducer sheath 100 and a dilator 200. The introducer assembly 1 is a medical instrument percutaneously inserted into a living body lumen (for example, an artery running through a limb such as the radial and femoral arteries) in order to insert various medical devices for diagnosis and treatment (for example, a diagnostic imaging catheter, a balloon catheter, or the like) up to a lesion portion in the body. The introducer sheath 100 is placed in the living body lumen prior to the device to be inserted and functions as an access route between the outside of the body and the inside of the living body lumen.

<Introducer Sheath>

Figure 2:
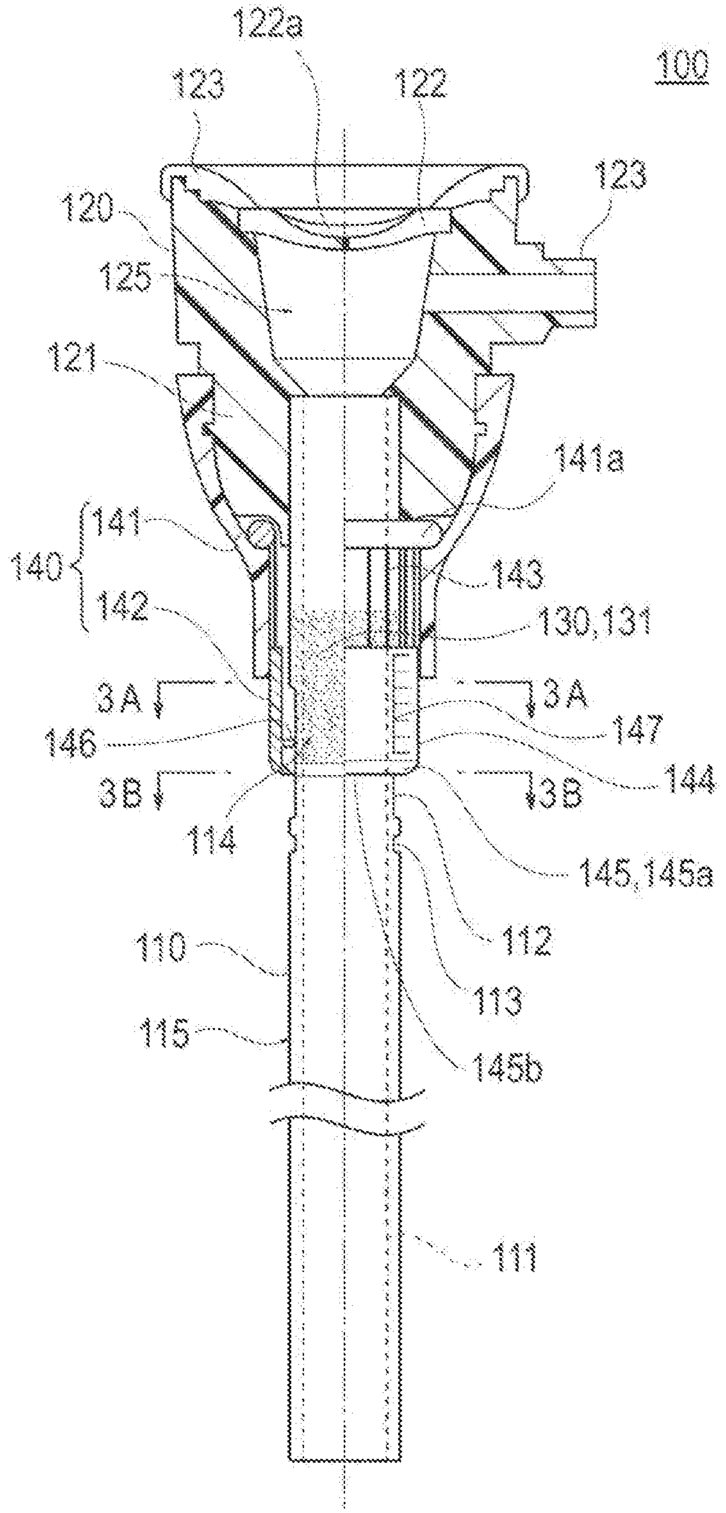
FIG. 2 is a partial cross-sectional view along the axial direction of the introducer sheath according to the first embodiment.

The introducer sheath 100 will be described. As illustrated in FIGS. 1 and 2, the introducer sheath 100 has the catheter main body 110 percutaneously inserted into the living body lumen (for example, a blood vessel V illustrated in FIG. 6A) with respect to a patient, a hub 120 fixed to the proximal portion of the catheter main body 110, a drug portion or drug covered region 130 disposed on an outer surface 115 of the catheter main body 110 closer to the distal side than the hub 120 (i.e., the drug portion 130 extends distally of the distal end of the hub 120), and a support member 140 disposed on the distal side of the hub 120 and covering the drug portion 130.

The introducer sheath 100 can be used to insert various medical instruments such as a dilator main body 210 of the dilator 200, a catheter, and a guide wire into the blood vessel V, which is a living body lumen, via a lumen 111 (see FIG. 2) of the catheter main body 110.

<Catheter Main Body>

As illustrated in FIG. 2, the catheter main body 110 is configured as a hollow tubular member having the lumen 111 extending in the axial direction. Opening portions for communication between the lumen 111 and the outside are respectively provided at the distal end and the proximal end of the catheter main body 110. That is, the catheter main body 110 includes open distal and proximal ends.

Examples of the constituent material from which the catheter main body 110 may be fabricated include polymer materials such as polyolefin (for example, polyethylene, polypropylene, polybutene, ethylene-propylene copolymer, ethylene-vinyl acetate copolymer, ionomer, or a mixture of two or more thereof), polyolefin elastomer, crosslinked polyolefin, polyvinyl chloride, polyimide, polyimide elastomer, polyester, polyester elastomer, polyurethane, polyurethane elastomer, fluororesin (for example, polytetrafluoroethylene or tetrafluoroethylene-ethylene copolymer), polycarbonate, polystyrene, polyacetal, polyimide, polyetherimide, and polyetheretherketone and mixtures thereof.

In addition, the outer surface 115 of the catheter main body 110 is provided with a groove portion (groove) 112 provided along the axial direction of the catheter main body 110 and closer to the distal side than the attachment position of the hub 120 (i.e., the groove 112 is distal of the hub 120).

The groove portion 112 is a recessed groove provided along the axial direction of the catheter main body 110. The groove portion 112 regulates the movement direction at a time when a covering member 142 (described later) of the support member 140 moves relative to the catheter main body 110 along the axial direction.

The groove portion 112 functions as a first engaging portion engaging with a protrusion portion 146 (second engaging portion) provided on a main body portion 144 of the covering member 142. The groove portion 112, which is the first engaging portion, blocks the rotation of the covering member 142 in the circumferential direction of the catheter main body 110 by engaging with the protrusion portion 146, which is the second engaging portion. The covering member 142 is prevented from rotating in conjunction with the rotation operation of a base portion 141 by the engagement state of the groove portion 112 and the protrusion portion 146. Accordingly, even if the drug portion 130 is exposed by the rotation operation of the base portion 141, the covering member 142 does not rotate in the circumferential direction of the catheter main body 110, and thus an adverse effect (such as twisting) on a puncture site P (see FIG. 6A) does not arise.

The axial length of the groove portion 112 is set to a distance at which the covering member 142 is capable of moving such that the drug portion 130 is exposed to the puncture site P and around the puncture site P at least in a state where the catheter main body 110 is placed in a living body tissue W. This length of the groove portion 112 is equivalent to a length at which the covering member 142 is capable of moving from a predetermined movement start position S to a movement end position E (see FIGS. 4A and 4B).

Figure 3A:
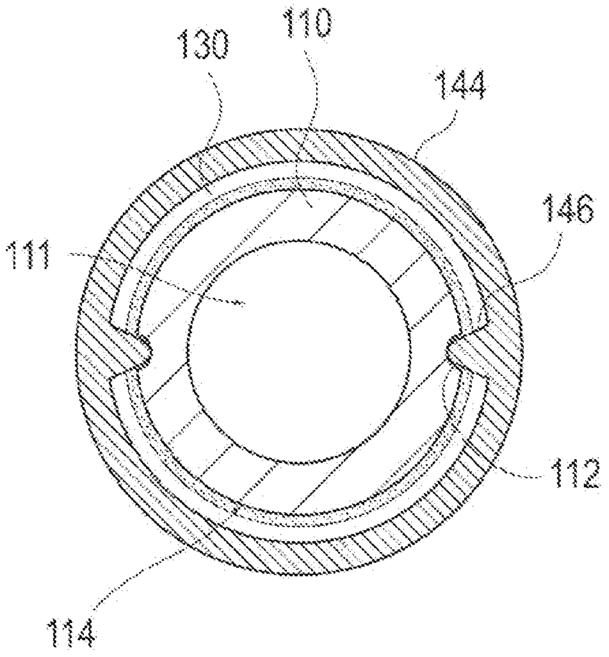
FIG. 3A is a cross-sectional view along the section line 3A-3A illustrated in FIG. 2.

As illustrated in FIG. 3A, as an example, the groove portion 112 is provided in two places with respect to the outer surface 115 of the catheter main body 110. The groove portion 112 may have a configuration in which the movement direction of the covering member 142 can be regulated in the axial direction of the catheter main body 110 and the rotation of the covering member 142 in the circumferential direction of the catheter main body 110 can be blocked. Accordingly, one or more groove portions (grooves) 112 may be provided in at least the catheter main body 110. However, from the viewpoint of smoothly moving the covering member 142, providing a plurality of the groove portions (grooves) 112 is more preferable than providing one groove portion 112 because the movement of the covering member 142 is stable in the former case. In addition, in a case where the plurality of groove portions 112 are provided, it is preferable that the groove portions 112 are provided at equal intervals along the circumferential direction of the catheter main body 110. In addition, as shown in FIG. 3A, when two grooves 112 are provided, two protrusions 146 are also provided, each of which engages a respective one of the grooves 112.

It should be noted that the cross-sectional shape of the groove portion 112 along the width direction can be formed in, for example, a semi-circular shape, a U shape, or a rectangular shape but is not limited thereto. The depth of the groove portion 112 is not particularly limited insofar as the depth is smaller than the thickness of the tube wall of the catheter main body 110.

The catheter main body 110 has a recess portion (recess) 113 disposed closer to the distal side than a disposition region 114 where the drug portion 130 is disposed (i.e., the recess 113 is distal of the distal end of the region 114 of the drug portion 114).

Figure 3B:
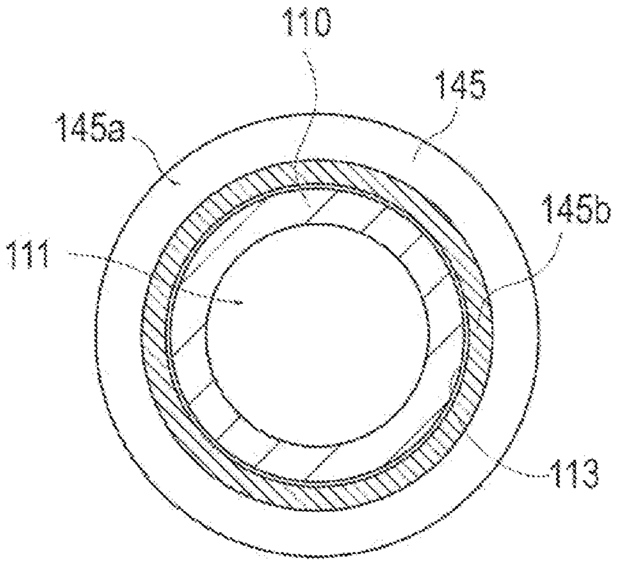
FIG. 3B is a cross-sectional view along the section line 3B-3B illustrated in FIG. 2.

The recess portion 113 is a groove recessed from the outer surface 115 of the catheter main body 110 toward the axial center along the circumferential direction of the catheter main body 110. As illustrated in FIG. 3B, a distal portion 145 of the covering member 142 is fitted into the recess portion 113 in a state before the rotation operation of the base portion 141 (that is, a state where the covering member 142 is positioned at the movement start position S).

The cross-sectional shape of the recess portion 113 along the axial direction of the catheter main body 110 is not particularly limited. However, considering the slidability of the covering member 142 (a distal end 145*b* in particular), the recess portion 113 preferably has a shape with a smoothly inclined surface such as a semi-circular shape and a U shape. As a result, when the covering member 142 moves from the movement start position S toward the movement end position E, the distal end 145*b* is capable of smoothly moving without being caught on the inner surface of the recess portion 113.

In addition, the catheter main body 110 has the disposition region 114, where the drug portion 130 is disposed, on the outer surface 115.

The disposition region 114 is where the drug portion 130 is disposed. The disposition region 114 is set to a position where a drug 131 held by the drug portion 130 is exposed at the puncture site P and around the puncture site P when the introducer sheath 100 is placed at the puncture site P and the state of covering of the drug portion 130 with the covering member 142 is released. Accordingly, the disposition region 114 and the drug portion 130 are substantially equivalent in area.

As illustrated in FIG. 2 or FIG. 3A, the disposition region 114 may be, for example, located inside the groove portion 112 in the outer surface 115 of the catheter main body 110 (bottom surface, inner wall surface), on the outer surface 115 of the catheter main body 110 between the adjacent groove portions 112, or the like. In addition, the disposition region 114 may be located inside a dedicated groove separately provided for disposing the drug portion 130 in or on the catheter main body 110. In any case, the disposition region 114 is set to a position on at least a part of the outer surface 115 of the catheter main body 110 covered with the covering member 142 in a state before the rotation operation of the base portion 141. As a result, the drug portion 130 disposed in the disposition region 114 is not exposed in the living body tissue W (for example, the subcutaneous tissue of the skin) unless the covering member 142 moves away from the movement start position S.

<Hub>

As illustrated in FIG. 2, the hub 120 is connected to the catheter main body 110. The hub 120 has a housing 121 fixed to the proximal portion of the catheter main body 110. The housing 121 has an internal space 125 inside, and the internal space 125 communicates with the lumen 111 of the catheter main body 110. A side port 124 communicating with the lumen 111 of the catheter main body 110 is provided on the side of the housing 121.

The constituent material from which the housing 121 may be fabricated is not particularly limited, but a hard material such as a hard resin is suitable. Specific examples of the hard resin include polyolefin such as polyethylene and polypropylene, polyamide, polycarbonate, and polystyrene.

A valve body 122 is disposed in the internal space 125 of the hub 120. The valve body 122 prevents the body fluid (such as blood) that has flowed into the lumen 111 of the catheter main body 110 from leaking out of the hub 120.

The valve body 122 is configured by an elastic member formed with a slit 122*a* through which the dilator main body 210 and various medical devices can be inserted. The valve body 122 can be configured to have, for example, a substantially elliptical disk shape. The valve body 122 is fixed to the hub 120 by fitting a predetermined cap 123 into the proximal portion of the hub 120.

The constituent material for the valve body 122 is not particularly limited, and examples thereof include silicone rubber, latex rubber, butyl rubber, and isoprene rubber, which are elastic members. It should be noted that the valve body 122 is not particularly limited as to the specific shape, the structure of the slit 122*a*, and so on.

The cap 123 is fitted to the proximal portion of the hub 120 so as to surround a part of the outer peripheral surface of the hub 120. The cap 123 may have, for example, a structure fixed to the hub 120 inside the hub 120. In addition, the fixing of the cap 123 to the hub 120 is not limited only to fitting and may be, for example, screwing, bonding, or the like.

As illustrated in FIG. 1, one end portion of a tube 150 can be connected to the side port 124 provided on the side of the housing 121. A three-way stopcock 160 or the like can be connected to the other end portion of the tube 150. It should be noted that the hub 120 may be configured to be fixedly connected to the catheter main body 110 or detachably connected to the catheter main body 110 by fitting, screwing, or the like.

<Drug Portion>

The drug portion 130 is disposed on at least a part of the outer surface 115 of the catheter main body 110. Specifically, the drug portion 130 is disposed in the disposition region 114 on the outer surface 115 of the catheter main body 110. FIG. 3A illustrates a state where the drug portion 130 is disposed over substantially the entire circumference of the outer surface 115 of the catheter main body 110. The drug portion 130 holds (contains) the predetermined drug 131.

The drug 131 has a hemostatic agent capable of treating a wound site in the living body tissue W. The type of the hemostatic agent is not particularly limited. For example, thromboplastin, thrombin, menadione sodium bisulfite, acetomenaphthone, ε-aminocaproic acid, tranexamic acid, sodium carbazochrome sulfonate, adrenochrome monoaminoguanidine methanesulfonate, and so on can be used as the hemostatic agent. In addition, a commercially available surgical hemostatic agent such as MATSUDAITO (registered trademark) manufactured by Sanyo Chemical Industries, Ltd. may be used as the hemostatic agent.

The drug portion 130 can be configured by disposing the drug 131 that is powder, gel, or solid in the disposition region 114 on the outer surface 115 of the catheter main body 110. In addition, the drug portion 130 may be disposed in the disposition region 114 on the outer surface 115 of the catheter main body 110 by mixing the drug 131 that is a liquid or the like with another material to increase the viscosity. As for the drug portion 130, a mixture of the drug 131 and a biodegradable material such as gelatin may be prepared and disposed in the disposition region 114 on the outer surface 115 of the catheter main body 110. In addition, the drug portion 130 may be disposed on the outer surface 115 of the catheter main body 110 with an adhesive layer provided between the drug 131 and the outer surface 115 of the catheter main body 110 in the disposition region 114.

It is preferable that the drug portion 130 is, for example, disposed in a state of being covered with the covering member 142 with the introducer sheath 100 yet to be used. By disposing the drug portion 130 in this manner, the drug 131 in the drug portion 130 peeling off can be suppressed even in the event of contact between the outer surface 115 of the catheter main body 110 and another member or the like. In addition, the drug portion 130 is covered with the covering member 142, which can be moved relative to the catheter main body 110 by the rotation operation of the base portion 141, and thus the drug portion 130 can be exposed at any exposure timing.

<Support Member>

The support member 140 is connected to the hub 120 and mounted on the proximal portion of the catheter main body 110. The support member 140 suppresses the occurrence of kink, breakage, and the like in the catheter main body 110. As illustrated in FIG. 2, the support member 140 is externally fitted to the catheter main body 110 and the hub 120. The distal side of the support member 140 is disposed so as to surround a certain range of the proximal portion of the catheter main body 110. The proximal side of the support member 140 is disposed so as to surround a certain range of the distal side of the hub 120. The support member 140 may be detachably connected to the hub 120. In addition, insofar as the support member 140 is rotatable in the circumferential direction of the catheter main body 110, a part of the support member 140 may be fixed to the hub 120 to maintain the connection state.

The support member 140 has the base portion 141 rotatable in the circumferential direction of the catheter main body 110, the covering member 142 disposed so as to protrude from the distal end of the base portion 141 and cover the drug portion 130 while overlapping at least a part of the base portion 141 in the radial direction from the outer surface 115 of the catheter main body 110, and a connecting member 143 connecting the base portion 141 and the covering member 142.

The base portion 141 is provided so as to be rotatable along the circumferential direction of the catheter main body 110 with respect to the housing 121 at least in a state of covering the distal portion of the housing 121 of the hub 120. In the illustrated embodiment, the base portion 141 is a tubular piece having proximal and distal ends. As illustrated in FIG. 2, the base portion 141 is provided with a ring member 141*a* inside the base portion 141.

As illustrated in FIG. 2, the ring member 141*a* is disposed near the distal end of the housing 121 on the proximal portion of the catheter main body 110. The ring member 141*a* is connected to the proximal side of the covering member 142 via the connecting member 143. As a result, when an operator rotates the base portion 141 in a predetermined rotation direction, the base portion 141 is capable of smoothly transmitting a force to the connecting member 143 via the ring member 141*a*. As illustrated in FIG. 2, the ring member 141*a* may be a seal member such as an O-ring. The seal member is capable of preventing liquid (such as blood) infiltration into the support member 140 when an operator rotates the base portion 141 in a predetermined rotation direction. The base portion 141 is rotated in a predetermined rotation direction when the covering member 142 is moved from the movement start position S to the movement end position E.

The covering member 142 is disposed so as to partially protrude from the distal side of the base portion 141 so as to cover the drug portion 130 disposed in the disposition region 114 of the catheter main body 110. The covering member 142 has the main body portion 144 extending along the axial direction of the catheter main body 110 and covering the groove portion 112 in a state before the rotation operation of the base portion 141 and the distal portion 145 extending to the distal side from the main body portion 144 and positioned closer to the distal side than the drug portion 130 disposed on the catheter main body 110. In the illustrated embodiment, the covering member 142 is a cover having a longitudinal extent that axially overlaps with and covers the drug portion 130.

Figure 4A:
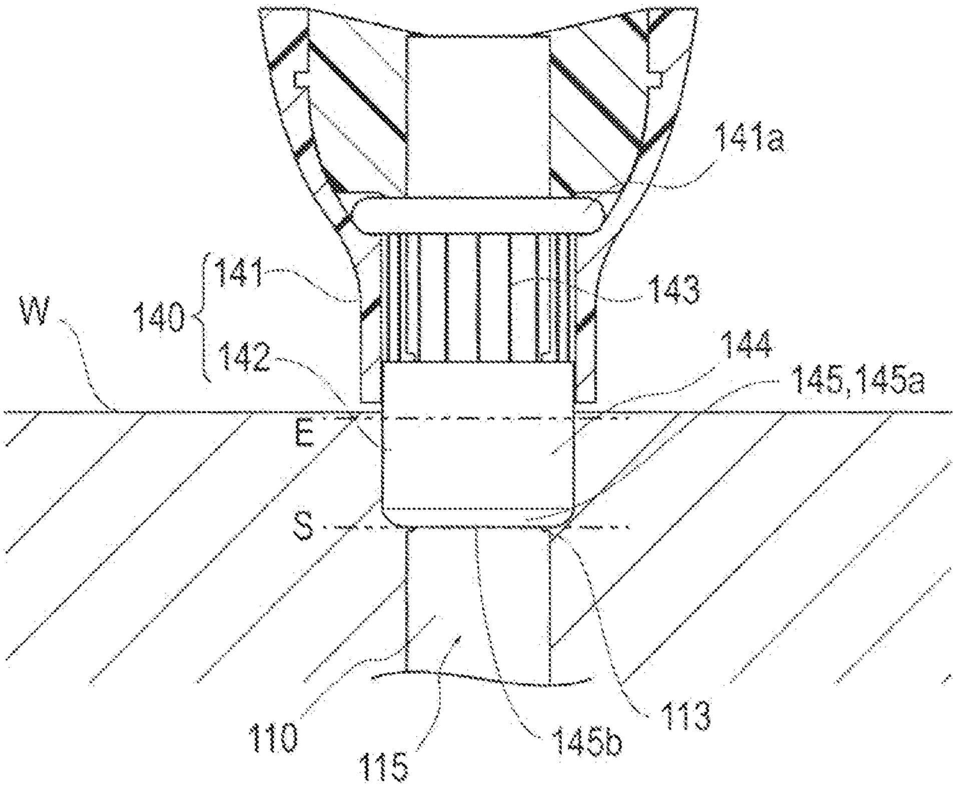
FIG. 4A is a partial cross-sectional view illustrating a state where a drug portion is yet to be exposed to a puncture site in the introducer sheath according to the first embodiment.
Figure 4B:
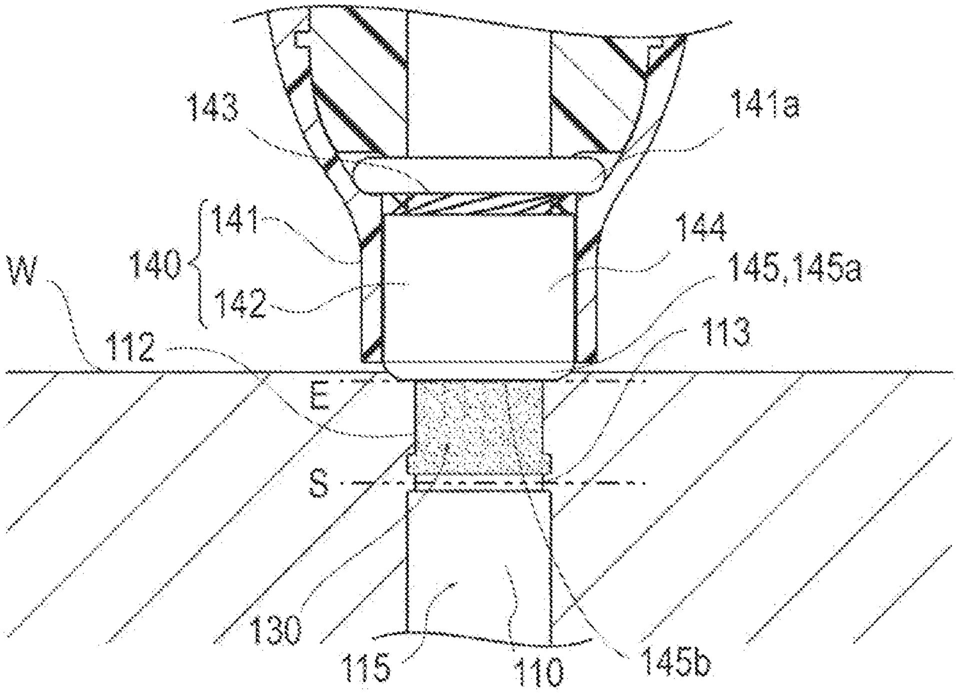
FIG. 4B is a partial cross-sectional view illustrating a state where the drug portion is exposed to the puncture site in the introducer sheath according to the first embodiment.

The covering member 142 covers the drug portion 130 in a state where the distal end 145*b* of the distal portion 145 is positioned at the movement start position S and exposes the drug portion 130 when the distal end 145*b* moves from the movement start position S to the movement end position E. As illustrated in FIGS. 4A and 4B, the movement start position S may be, for example, the position of the two-dot chain line on the distal side of the catheter main body 110, and the movement end position E may be, for example, the position of the two-dot chain line on the proximal side of the catheter main body 110.

It should be noted that the movement start position S and the movement end position E set on the outer surface 115 of the catheter main body 110 may be set to positions where the function of the covering member 142 is not impaired before and after the rotation operation of the base portion 141.

The covering member 142 is disposed in a state where at least the region protruding from the base portion 141 (protruding distally beyond the base portion 141) and covering the drug portion 130 is inserted in the living body tissue W. Accordingly, it is preferable that the covering member 142 is configured such that the outer diameter of the covering member 142 is larger than the outer diameter of the catheter main body 110 such that the effect of preventing the catheter main body 110 from coming off the living body tissue W can be obtained. That is, the catheter main body 110 is inhibited from being pulled out of the living body tissue W. In addition, the covering member 142 is preferably configured by a metal material or a fluorine-based resin harder than the material for the catheter main body 110 such that the outer diameter of the covering member 142 can be maintained and the covering member 142 can be smoothly inserted into the living body tissue W when the catheter main body 110 is inserted into the living body tissue W. It should be noted that as for the covering member 142, a surface roughness-increasing treatment (such as blasting) may be performed on a part or the whole of the outer surface of the main body portion 144 in order to obtain the effect of preventing the catheter main body 110 from coming off.

The main body portion 144 is disposed so as to overlap (axially overlap) at least a part of the base portion 141 in the radial direction from the outer surface 115 of the catheter main body 110. As illustrated in FIGS. 2 and 3A, the main body portion 144 is configured to have, for example, a hollow cylindrical shape (hollow tubular body) and is mounted so as to be movable along the axial direction with respect to the catheter main body 110. By adopting the hollow cylindrical shape, the covering member 142 has a substantially circular cross-sectional shape in a direction intersecting the axial direction as in the case of the catheter main body 110. Accordingly, the introducer sheath 100 can be disposed in a state where the clearance between the covering member 142 and the catheter main body 110 is smaller than in a shape such as a hollow prism shape. Accordingly, the introducer sheath 100 has the effect that the outer diameter decreases and the insertion resistance at the time of insertion is reduced.

In addition, the protruding protrusion portion 146 engaging with the groove portion 112 provided in the outer surface 115 of the catheter main body 110 is provided inside the main body portion 144. The protrusion portion 146 is provided at a position inside the main body portion 144 corresponding to the formation position of the groove portion 112 (that is, a position capable of engaging with the groove portion 112). Rotation of the covering member 142 in the circumferential direction of the catheter main body 110 is blocked by the protrusion portion 146 engaging with the groove portion 112. The protrusion portion 146 functions as the second engaging portion engaging with the groove portion 112 of the catheter main body 110.

The main body portion 144 is preferably disposed so as to cover the groove portion 112 in a state before the rotation operation of the base portion 141. When the introducer sheath 100 is inserted in the puncture site P in, for example, a configuration without the covering member 142, kink, buckling, or the like attributable to the groove portion 112 is likely to occur. On the other hand, by disposing the main body portion 144 of the covering member 142 so as to cover the groove portion 112, the catheter main body 110 can be improved in kink resistance and kink or buckling attributable to the groove portion 112 can be suppressed.

The distal portion 145 is disposed closer to the distal side than the drug portion 130 disposed on the catheter main body 110 in a state before the rotation operation of the base portion 141. In other words, the main body portion 144 is positioned closer to the proximal side of the catheter main body 110 than at least the distal portion 145 and is disposed in a state of covering the drug portion 130. Accordingly, the drug portion 130 does not come into contact with the living body tissue W or another member until the covering member 142 is moved by the rotation operation of the base portion 141.

The distal portion 145 is inclined toward the outer surface 115 of the catheter main body 110. Specifically, the distal portion 145 has a tapered surface 145*a* having a smooth R shape such that the outer circumference of the distal portion 145 becomes smaller from the proximal side toward the distal side.

When the covering member 142 is inserted into the puncture site P, the distal portion 145 first comes into contact with the skin that is the living body tissue W in the covering member 142, and thus the resistance from the skin is large. Accordingly, by the distal portion 145 being configured to be inclined toward the outer surface 115 of the catheter main body 110, the resistance acting on the distal portion 145 from the skin at the time of insertion into the puncture site P is reduced. Accordingly, the introducer sheath 100 is improved in insertability with respect to the puncture site P.

The distal end 145*b* of the distal portion 145 fits into the recess portion 113 provided in the catheter main body 110 in a state before the rotation operation of the base portion 141 (that is, a state where the covering member 142 is positioned at the movement start position S). The distal end 145*b* and the recess portion 113 come into close contact with each other, and thus blood infiltration into the covering member 142 is prevented when the introducer sheath 100 is placed in the living body lumen.

As illustrated in FIG. 2, the outer surface 115 of the covering member 142 may be provided with a marker portion 147 such as a graduated scale (for example, a scale with a graduation or interval of 0 to 5 mm) with which the amount by which the catheter main body 110 comes off or is moved can be visually recognized. As a result, an operator can easily know the degree of the introducer sheath 100 coming off or moving by visually recognizing the marker portion 147.

The material for the marker portion 147 is not particularly limited, and examples thereof include an oil-based colorant such as ink and a pigment-kneaded resin. In addition, the marker portion 147 is not limited to the scale memory and may have any shape with which an operator can grasp the degree of the catheter main body 110 coming off.

One end of the connecting member 143 is connected to the proximal side of the base portion 141, and the other end of the connecting member 143 is connected to the ring member 141*a* provided on the support member 140. The connecting member 143 is deformed such that the distance between the support member 140 and the covering member 142 decreases in accordance with the amount of rotation at the time of the rotation operation of the base portion 141 to move the covering member 142 from the movement start position S to the movement end position E. As illustrated in FIG. 2, the connecting member 143 may be configured by a linear member such as a wire as an example. The connecting member 143 is wound up toward the proximal side of the catheter main body 110 while being deformed by the rotation of the ring member 141*a* rotating in conjunction with the base portion 141. At this time, the connecting member 143 is deformed from a substantially straight state to a substantially spiral shape along the outer circumference of the catheter main body 110 by the rotation of the base portion 141 to pull up and move the covering member 142 to the proximal side of the catheter main body 110. The connecting member 143 is configured to be positioned between the support member 140 and the catheter main body 110. Accordingly, an operator does not come into contact with the connecting member 143 during the operation of the introducer sheath 100. Accordingly, even if the connecting member 143 is a deformable linear material, the introducer sheath 100 is capable of suppressing contact between an operator and the connecting member 143 attributable to his or her erroneous operation and is capable of preventing the covering member 142 from moving in conjunction with the connecting member 143.

FIGS. 4A, 4B, 5A and 5B illustrate states before and after the drug portion 130 is exposed with the introducer sheath 100 placed at the puncture site P.

Figure 5A:
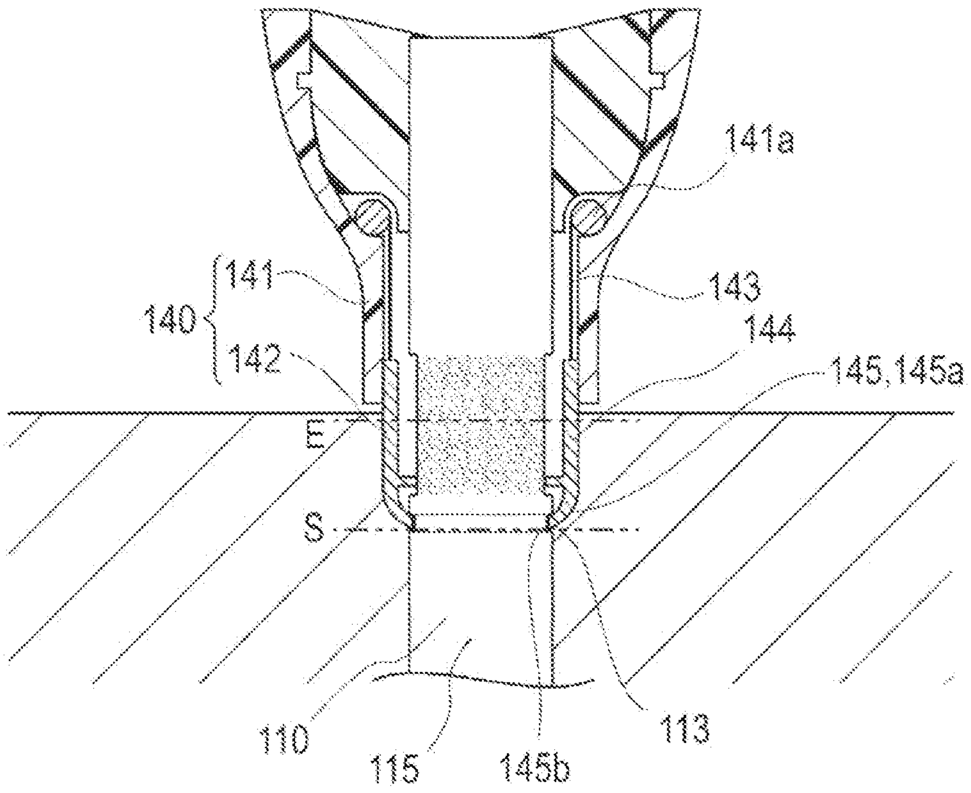
FIG. 5A is a partial cross-sectional view in which the main configuration of the introducer sheath illustrated in FIG. 4A is partially cut.
Figure 5B:
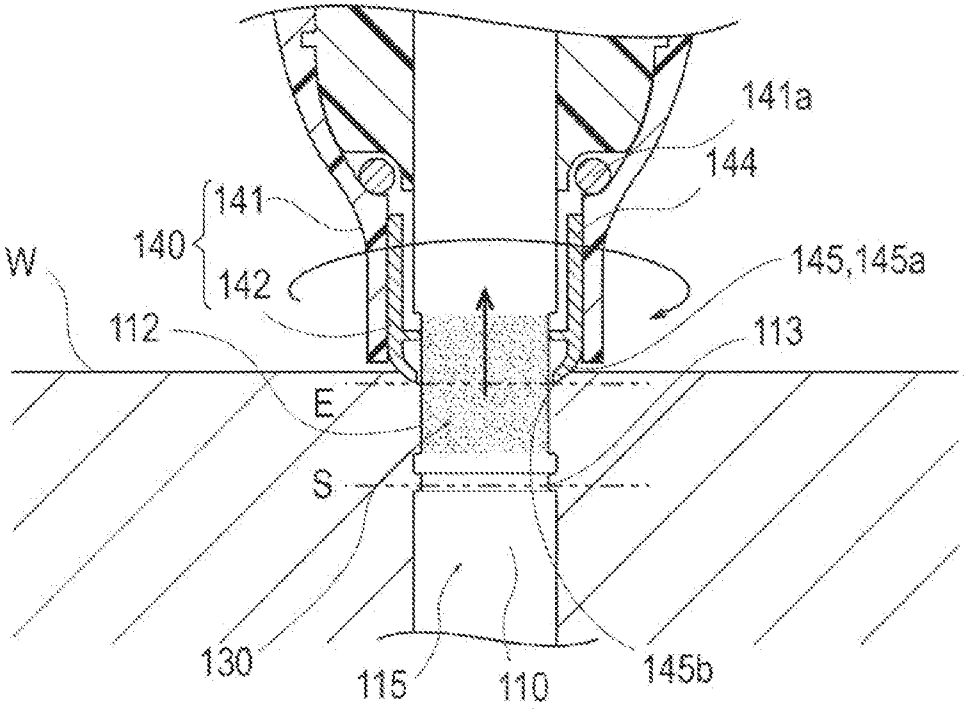
FIG. 5B is a partial cross-sectional view in which the main configuration of the introducer sheath illustrated in FIG. 4B is partially cut.

As illustrated in FIGS. 4A and 5A, since the base portion 141 is not rotated, the drug portion 130 is not in contact with the living body tissue W such as the skin or another member in a state of being covered with the covering member 142. An operator rotates the base portion 141 in a predetermined direction after a predetermined procedure is completed. Then, as illustrated in FIGS. 4B and 5B, the connecting member 143 is wound up and deformed with the rotation of the ring member 141*a* of the base portion 141 and the covering member 142 is moved (axially moved) upward in the drawing (to the proximal side of the catheter main body 110) by this deformation. As illustrated in FIGS. 4B and 5B, the drug portion 130 is exposed in the living body tissue W by the covering member 142 moving to the proximal side (in the proximal direction) of the catheter main body 110. It should be noted that the timing at which an operator rotates the base portion 141 in a predetermined direction may precede the completion of a predetermined procedure. For example, an operator may rotate the base portion 141 in a predetermined direction and expose the drug portion 130 in the living body tissue W during a predetermined procedure in view of the time of the drug 131 permeating the living body tissue W.

As described above, in the introducer sheath 100 according to the first embodiment, the covering member 142 with which the drug portion 130 is covered can be moved relative to the catheter main body 110 along the axial direction of the catheter main body 110 by rotating the base portion 141 of the support member 140 mounted on the catheter main body 110 in a predetermined direction. Accordingly, as for the drug portion 130, an operator can expose the drug portion 130 at a desired exposure timing by the simple operation of rotating the base portion 141. In addition, the catheter main body 110 does not move in the forward-backward direction even when the base portion 141 is rotated and thus does not adversely affect the puncture site P.

<Dilator>

As illustrated in FIG. 1, the dilator 200 has the dilator main body 210 insertable through the catheter main body 110 of the introducer sheath 100 and a dilator hub 220 configured to be connectable to the hub 120 of the introducer sheath 100.

The distal end of the dilator main body 210 has a tapered shape tapering toward the distal side. The dilator main body 210 has a length at which the distal end of the dilator main body 210 protrudes by a predetermined length from the opening portion provided at the distal end of the catheter main body 110 in a state where the dilator main body 210 is inserted through the lumen 111 of the catheter main body 110 of the introducer sheath 100. The dilator 200 can be used in order to prevent the catheter main body 110 from breaking or increase the diameter of the puncture site P when the catheter main body 110 of the introducer sheath 100 is inserted into the blood vessel V.

The constituent material from which the dilator main body 210 may be made is not particularly limited, and a hard material similar to that used in the related art as the dilator main body 210 can be suitably used. Specific examples of the constituent material include polyolefin such as polypropylene (P) and polyethylene (PE), nylon, polyester such as polyethylene terephthalate (PET), and fluorine-based polymer such as polyvinylidene fluoride (PVDF) and tetrafluoroethylene-hexafluoropropylene copolymer (FEP).

Next, an example of using the introducer sheath 100 will be described with reference to FIGS. 6A to 6E. The region surrounded by the dotted line in FIG. 6A corresponds to the puncture site P and the surrounding region.

Figure 6A:
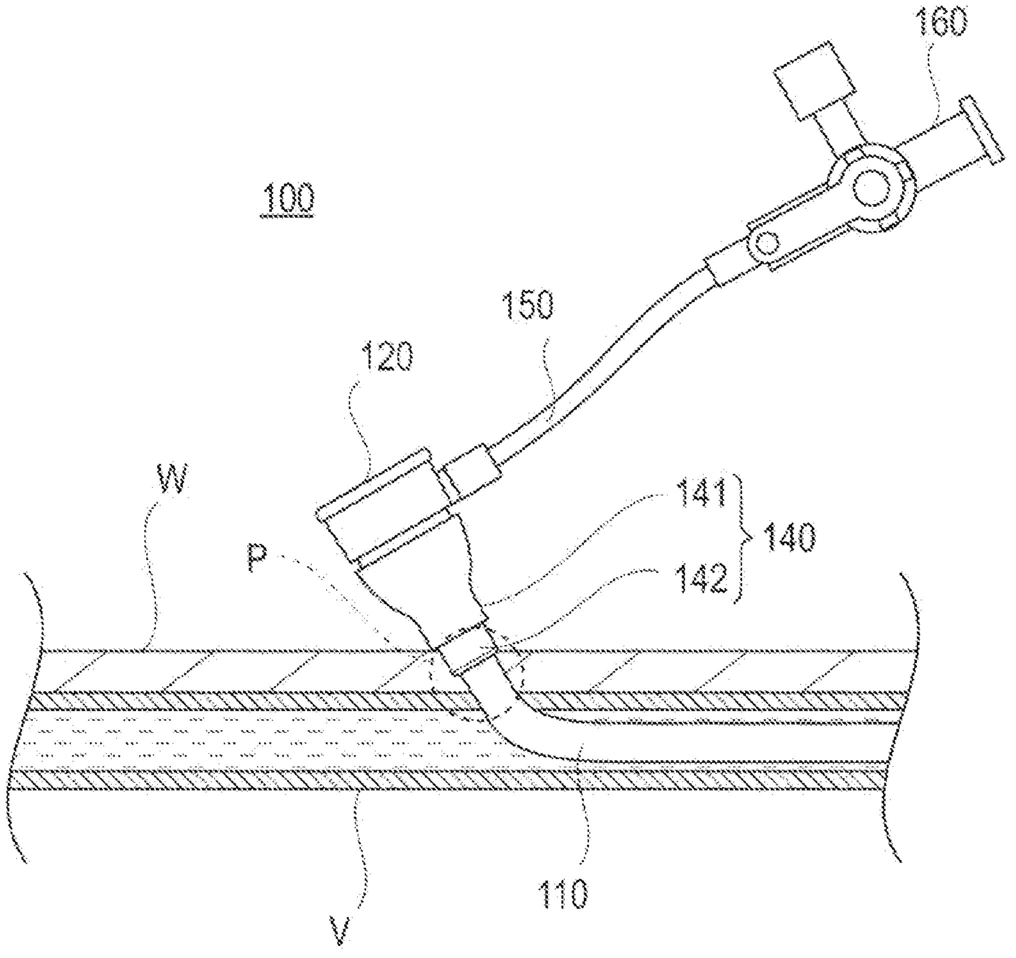
FIG. 6A is a conceptual diagram illustrating a state where the introducer sheath according to the first embodiment is inserted in a living body lumen.

FIG. 6A illustrates a state where, following the dilator 200 being assembled in the introducer sheath 100, and the catheter main body 110 of the introducer sheath 100 being percutaneously inserted into the blood vessel V via the puncture site P formed in a patient's limb, the dilator 200 is removed.

When the introducer sheath 100 is inserted into the blood vessel V, the distal portion 145 of the covering member 142 is in a state of being fitted with or into the recess portion 113. Accordingly, the clearance between the distal end 145*b* of the distal portion 145 and the outer surface 115 of the catheter main body 110 is extremely close to zero. As a result, when the introducer sheath 100 is inserted into the puncture site P, the covering member 142 is reduced in insertion resistance with respect to the puncture site P, and thus the insertion of the introducer sheath 100 is facilitated.

Figure 6B:
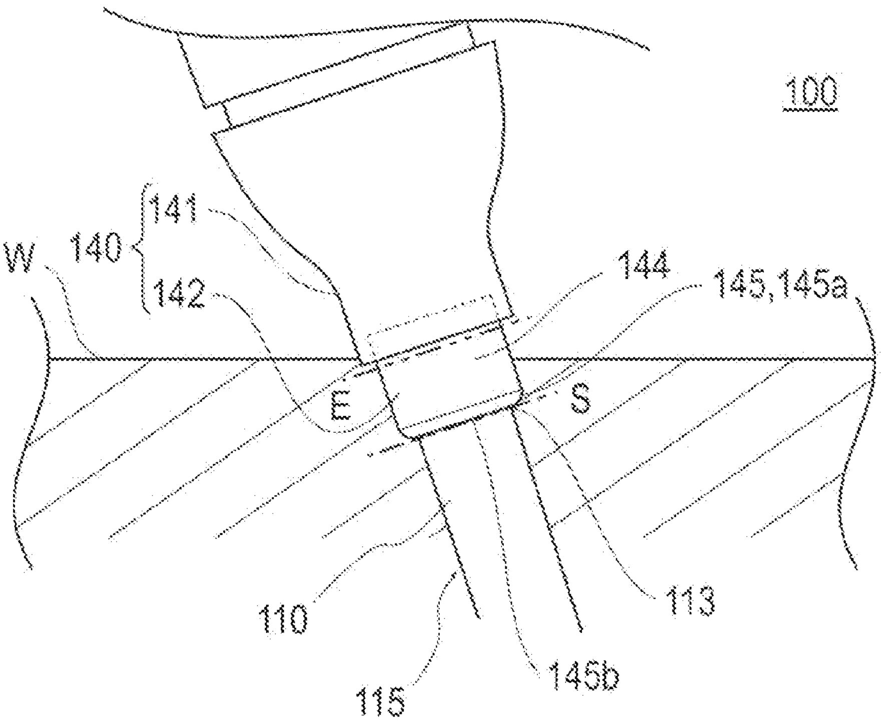
FIG. 6B is a conceptual diagram illustrating a state where a covering member is inserted in the puncture site.

FIG. 6B is an enlarged view of the periphery of the support member 140 of the introducer sheath 100 that is placed in the living body lumen. As illustrated in FIG. 6B, the base portion 141 is not rotated, and thus the drug portion 130 is covered with the covering member 142. Accordingly, the drug portion 130 is not eluted in the living body tissue W.

Figure 6C:
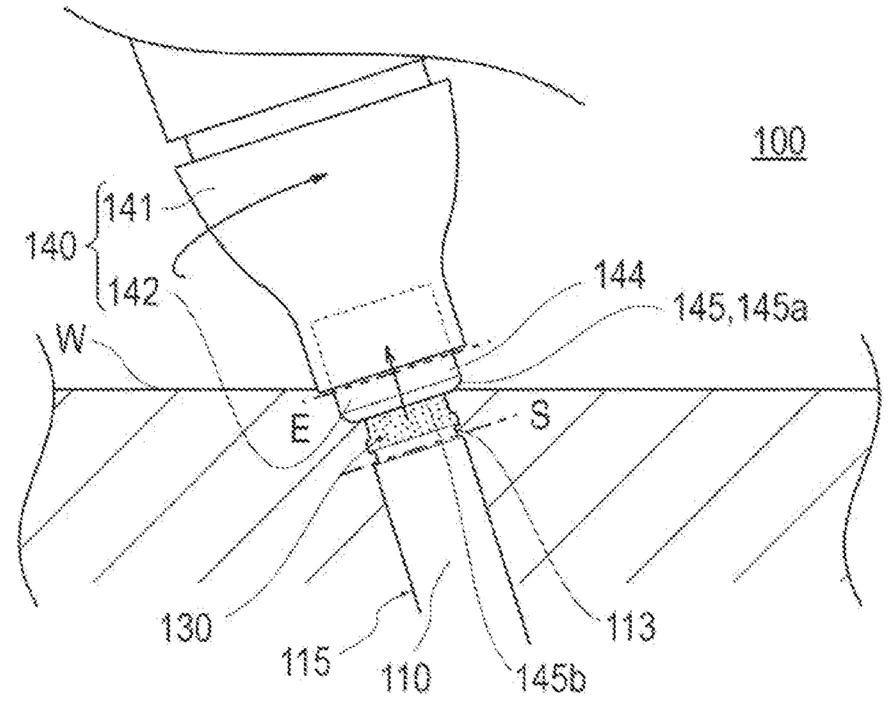
FIG. 6C is a conceptual diagram illustrating a state where the covering member inserted in the puncture site has begun to move from a movement start position.

An operator rotates the base portion 141 in a predetermined direction when a predetermined procedure is completed and an exposure timing of the drug portion 130 is reached. As illustrated in FIG. 6C, the covering member 142 begins to move to the proximal side of the catheter main body 110 by this rotation operation. At this time, by the rotation operation of the base portion 141, the connecting member 143 is wound up by the ring member 141*a* rotating in conjunction with the base portion 141 and moves the covering member 142 from the movement start position S to the proximal side of the catheter main body 110. In addition, as illustrated in FIG. 6C, the drug portion 130 begins to be gradually exposed to the living body tissue W as the covering member 142 is moved in the proximal direction by the rotation operation of the base portion 141.

Figure 6D:
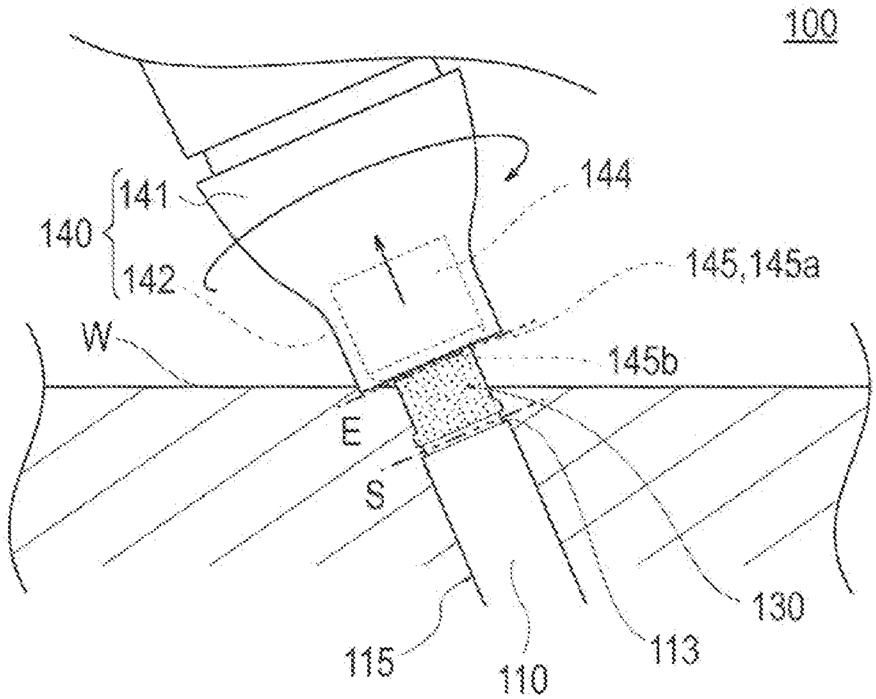
FIG. 6D is a conceptual diagram illustrating a state where the covering member inserted in the puncture site has moved to a movement end position.

As illustrated in FIG. 6D, the operator rotates the base portion 141 to move the covering member 142 from the movement start position S to the movement end position E. As a result, the drug portion 130 covered with the covering member 142 is substantially completely exposed in the living body tissue W. It should be noted that until the FIG. 6D position is reached from the FIG. 6C position, the operator can adjust the amount of rotation of the base portion 141 to control the degree of the state of exposure of the drug portion 130. As a result, the operator can give an appropriate treatment to the puncture site P by the amount of elution of the drug 131 with respect to the living body tissue W being adjustable based on the degree of exposure of the drug portion 130 with respect to the living body tissue W.

Figure 6E:
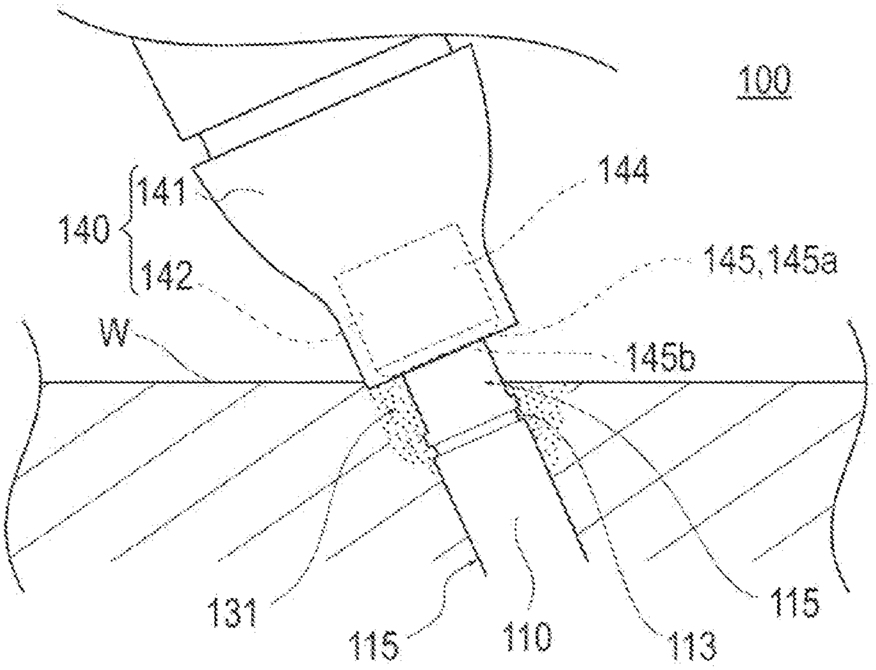
FIG. 6E is a conceptual diagram illustrating a state where the drug portion is exposed and absorbed around the puncture site.

Then, as illustrated in FIG. 6E, the drug 131 in the drug portion 130 exposed in the living body tissue W is eluted at the puncture site P and around the puncture site P. The drug 131 eluted in the living body tissue W is absorbed by the living body tissue W at the puncture site P and around the puncture site P to treat the wound and stop bleeding.

Next, another embodiment of the medical elongated body according to the disclosure here will be described. In the following second embodiment and modification example of the second embodiment, the same reference numerals are given to constituent elements having the same functions as those of the first embodiment with a detailed description of such elements not being repeated. In addition, in the second embodiment and the modification example of the second embodiment, configurations, members, methods of use, and so on not particularly mentioned may be the same as those in the embodiment described above.

Second Embodiment

The medical elongated body according to the second embodiment will be described with reference to FIGS. 7 to 13 as appropriate. In the second embodiment, the medical elongated body is an example applied to the introducer sheath 300 forming a part of the introducer assembly 1.

The introducer sheath 300 according to the second embodiment is different from the introducer sheath 100 according to the first embodiment mainly in the following configurations. In the introducer sheath 300 according to the second embodiment, a covering member 342 covering the drug portion or drug covered region 130 is different in configuration from the covering member 142 of the introducer sheath 100. In addition, the introducer sheath 300 is different from the introducer sheath 100 in disposition position of the disposition region 114 of the drug portion 130. Further, by including the covering member 342, the introducer sheath 300 does not require the configuration of the connecting member 143 used in connecting the groove portion 112 and the recess portion 113 provided in the catheter main body 110 and the ring member 141*a*.

The introducer sheath 300 according to the second embodiment will be described. The introducer assembly 1 is illustrated in FIG. 7, and FIG. 8 is a cross-sectional view of the introducer sheath 300 (partial cross-sectional view along the axial direction).

Figure 7:
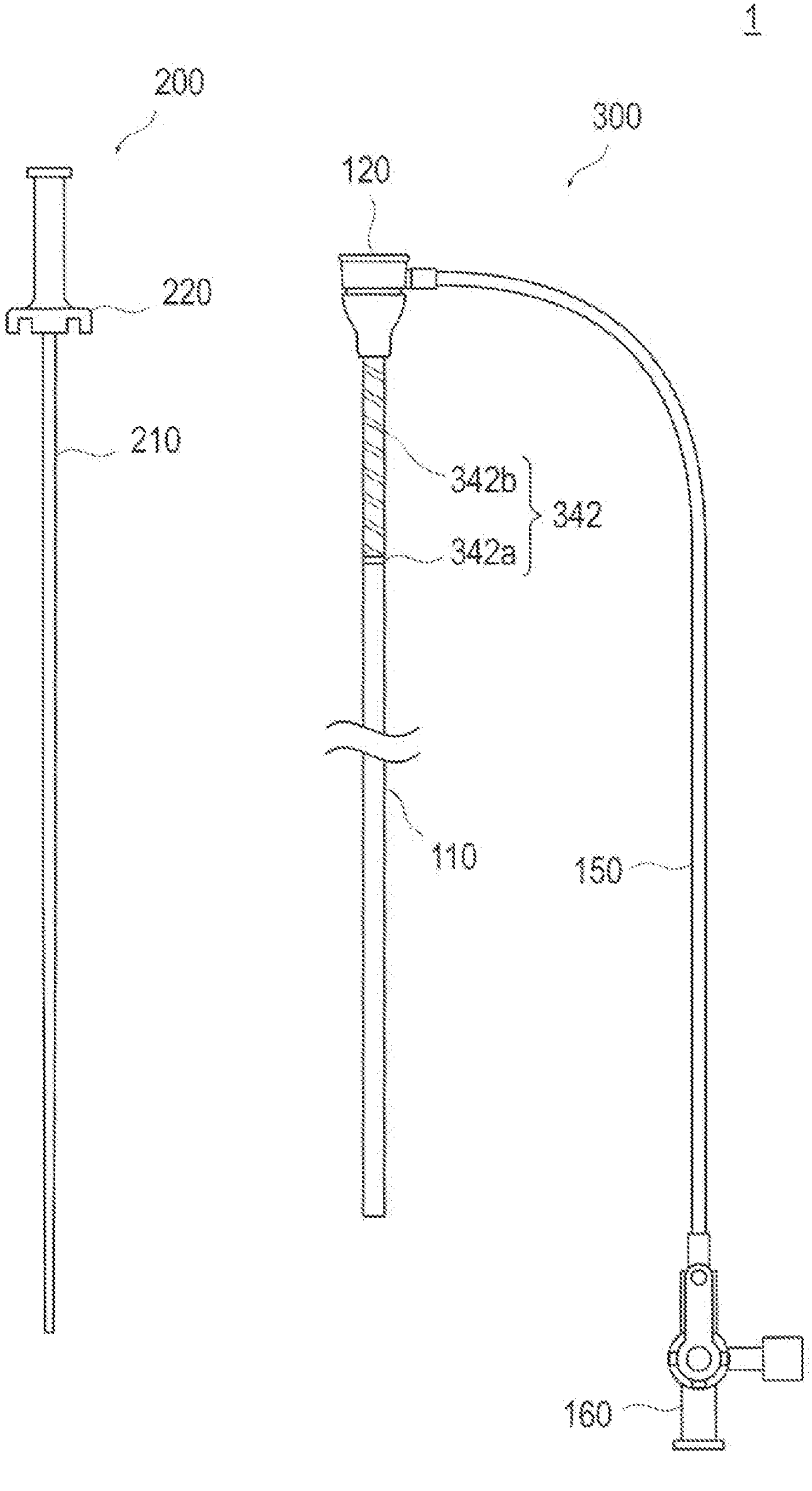
FIG. 7 is a plan view illustrating the configuration of an introducer assembly including an introducer sheath that is a medical elongated body according to a second embodiment.
Figure 8:
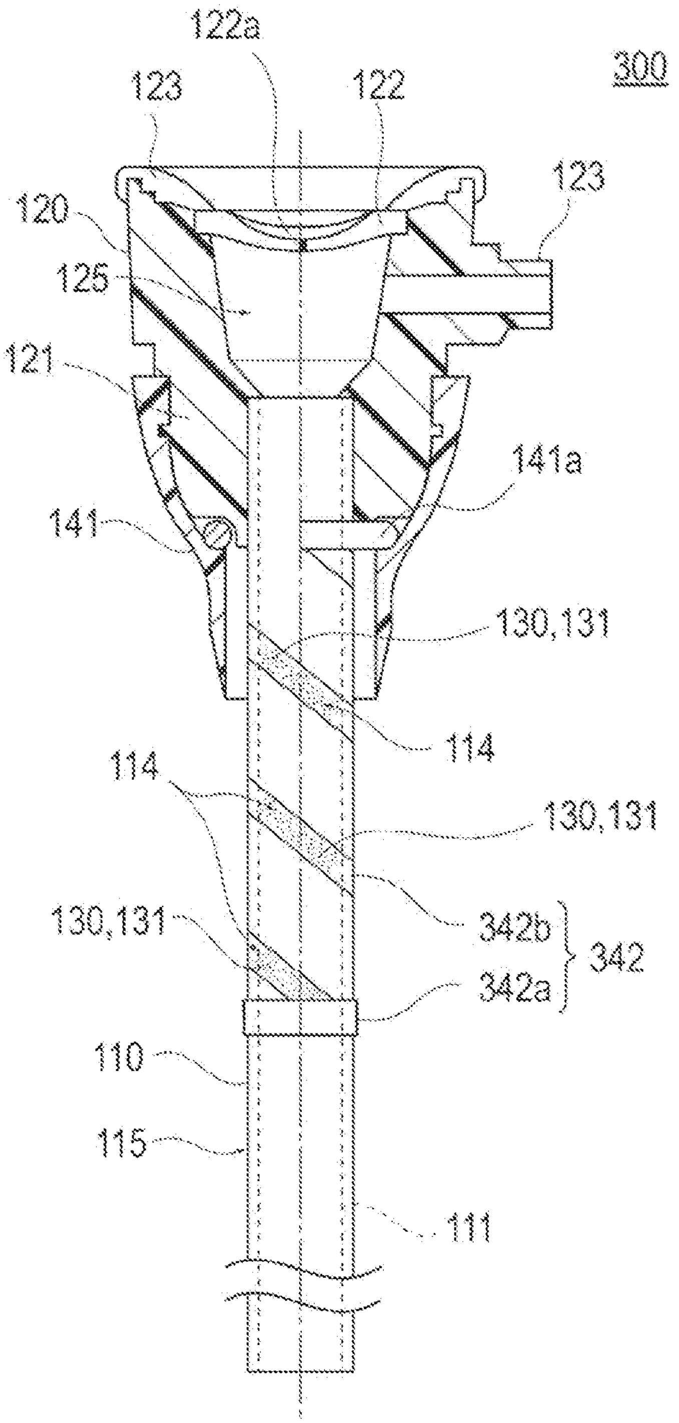
FIG. 8 is a partial cross-sectional view along the axial direction of the introducer sheath according to the second embodiment.

As illustrated in FIGS. 7 and 8, the introducer sheath 300 according to the second embodiment includes the covering member 342 covering the drug portion 130 in a state before the rotation of the base portion 141. The covering member 342 forms a part of the support member, together with the base portion 141.

The covering member 342 has a distal member 342*a* disposed closer to the distal side of the catheter main body 110 than the disposition region 114 where the drug portion 130 is disposed (the distal member 342*a* is located distal of the disposition region 114) and a band-shaped member 342*b* covering the drug portion 130 in a state before the rotation of the base portion 141.

Figure 13A:
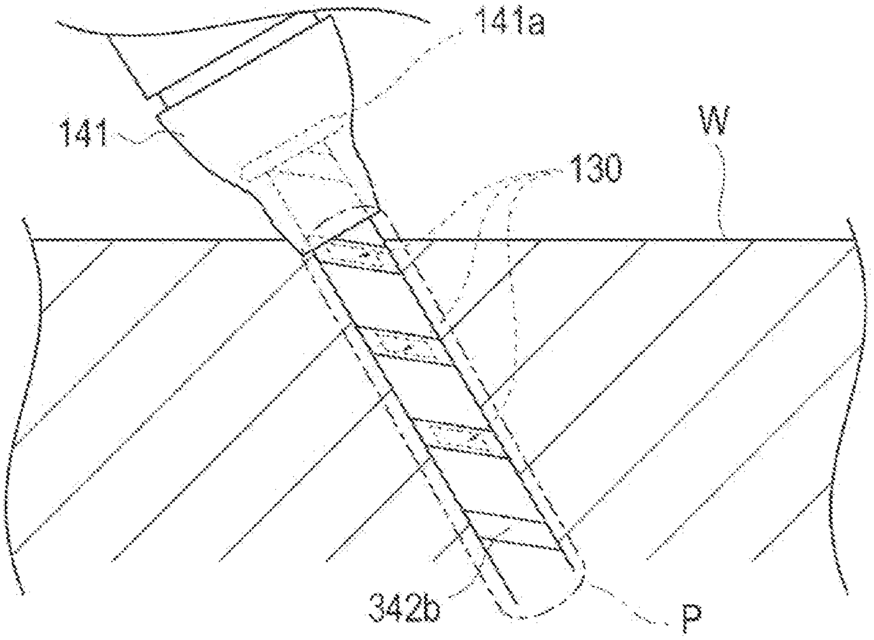
FIG. 13A is a conceptual diagram illustrating a state where the introducer sheath according to the second embodiment is placed in a living body.

The distal member 342*a* is attached to the outer surface 115 of the catheter main body 110 to limit at least the movement of the band-shaped member 342*b* to the distal side when the introducer sheath 300 is inserted into the puncture site P (see FIG. 13A). As an example, the distal member 342*a* may be configured by an annular member fitted with respect to the outer circumference (outer circumferential surface) of the catheter main body 110. In addition, it is preferable that the outer diameter of the distal member 342*a* is formed so as to be approximately equal to the outer diameter of the catheter main body 110 at the time of fitting to the catheter main body 110. As a result, the distal member 342*a* can be smoothly inserted with the insertion resistance of the distal member 342*a* received when the introducer sheath 300 is inserted in the puncture site P kept low. Further, in order to reduce the insertion resistance of the introducer sheath 300, the distal member 342*a* may be configured such that the upper surface of the distal portion of the distal member 342*a* is inclined toward the outer surface 115 of the catheter body 110.

It is preferable that the inner diameter of the distal member 342*a* is slightly smaller than the outer diameter of the catheter main body 110. At this time, the distal member 342*a* is fixed to the catheter main body 110, while the lumen

111 of the catheter main body 110 is maintained, by reducing the wall thickness of a part of the catheter main body 110 and fitting the distal member 342*a* to the wall thickness-reduced part. As a result, the position of the distal member 342*a* is fixed when the distal member 342*a* is press-fitted and fitted on the catheter main body 110, and thus a positional deviation of the band-shaped member 342*b* is prevented when the introducer sheath 300 is inserted in the puncture site P. The band-shaped member 342*b* does not deviate due to the insertion resistance at the time of inserting the introducer sheath 300 into the puncture site P, and thus the covering state of the drug portion 130 is maintained. In addition, the lumen 111 of the catheter main body 110 can also be maintained even when the distal member 342*a* is fixed to the catheter main body 110.

The band-shaped member 342*b* is configured by a band-shaped body having a predetermined length and made of a material having a predetermined width dimension such that the drug portion 130 can be covered. In the illustrated embodiment, the band-shaped member 342*b* is a cover having a longitudinal extent that axially overlaps with and covers the drug portion 130. FIGS. 7 and 8 also show that the band-shaped member 342*b* may be spirally-configured or helically-configured with axially spaced-apart adjacent winding. One end side (distal side) of the band-shaped member 342*b* is connected to the distal member 342*a*, and the other end side (proximal side) of the band-shaped member 342*b* is connected to the ring member 141*a*. The material configuring the band-shaped member 342*b* is not particularly limited. For example, the material configuring the band-shaped member 342*b* can be configured from a metal material such as SUS and NiTi or a resin material such as amide resin and fluororesin (ETFE, PTFE) in view of slidability with respect to the catheter main body 110. In addition, in a case as illustrated in FIG. 11, a metal elastic material such as shaped NiTi or a resin elastic material such as silicone rubber may be used as the material configuring the band-shaped member 342*b*.

As illustrated in FIG. 8, the band-shaped member 342*b* is wound in a substantially spiral shape around the outer surface 115 of the catheter main body 110. When wound around the catheter main body 110, the band-shaped member 342*b* is wound with a predetermined tension applied. As the ring member 141*a* is rotated by the rotation operation of the base portion 141, the applied tension is gradually released and the band-shaped member 342*b* moves relative to the catheter main body 110.

It should be noted that the interval of the band-shaped member 342*b* making a circle around the catheter main body 110 is not particularly limited insofar as a circle is made so as to correspond to the disposition position of the drug portion 130. In addition, the width dimension of the band-shaped member 342*b* may be at least a dimension at which the drug portion 130 provided in the catheter main body 110 is covered.

In addition, in the introducer sheath 300 according to the second embodiment, the disposition region 114 is set to a position where covering with the band-shaped member 342*b* is possible before the rotation operation of the base portion 141. The drug portion 130 disposed in the disposition region 114 may be directly disposed on the outer surface 115 of the catheter main body 110 or may be disposed inside a groove with the groove provided in the outer surface 115 as illustrated in, for example, FIG. 11A.

FIGS. 9A, 9B, 10A and 10B illustrate states before and after the release of the tension applied to the band-shaped member 342*b*.

Figure 9A:
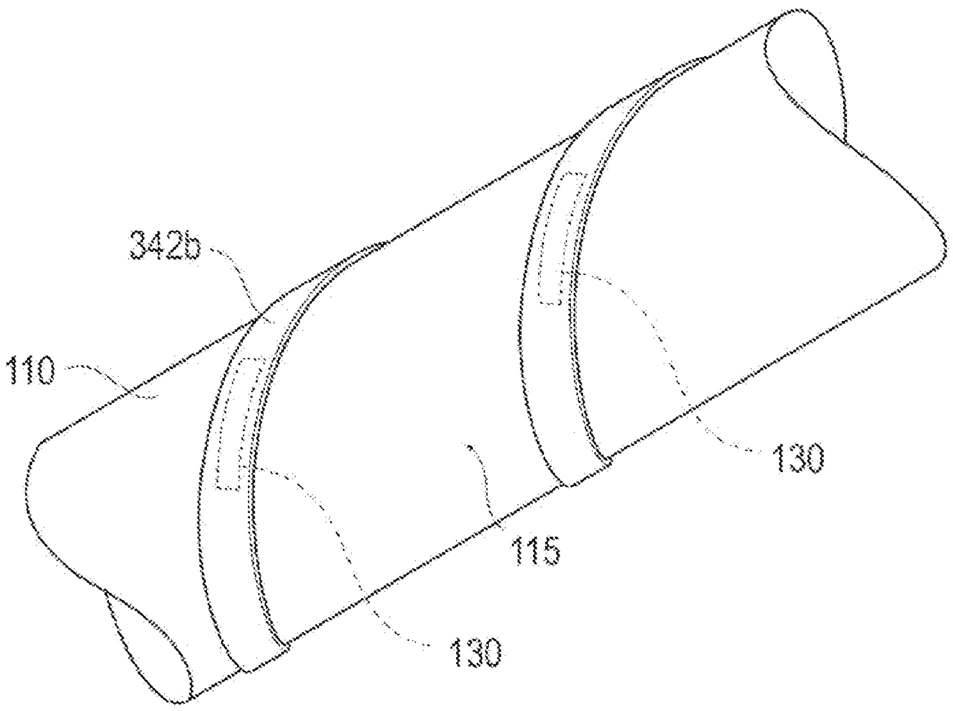
FIG. 9A is a schematic perspective view illustrating a state where a drug portion is covered with a band-shaped member of the introducer sheath according to the second embodiment.
Figure 9B:
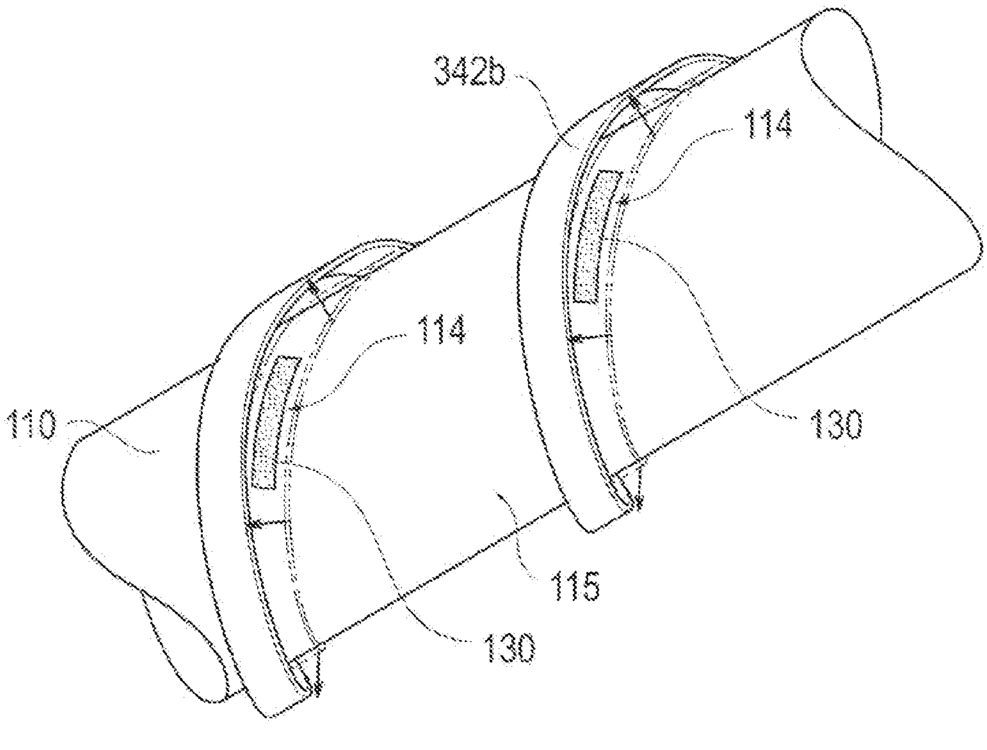
FIG. 9B is a schematic perspective view illustrating a state where the band-shaped member illustrated in FIG. 9A is moved in a first movement mode and the drug portion is exposed.

FIG. 9A illustrates a state where the drug portion 130 is covered with the band-shaped member 342*b* wound around the outer surface 115 of the catheter main body 110. FIG. 9B illustrates a state where the covering state of the band-shaped member 342*b* illustrated in FIG. 9A is released as the base portion 141 rotates.

As illustrated in FIG. 9A, the band-shaped member 342*b* is wound around the outer surface 115 of the catheter main body 110 so as to cover the disposition region 114 where the drug portion 130 is disposed in a state before the base portion 141 is rotated. In the state illustrated in FIG. 9A, the drug portion 130 is covered with the band-shaped member 342*b*, and thus the drug portion 130 does not come into contact with the living body tissue W and another member.

As illustrated in FIG. 9B, when the base portion 141 is rotated by an operator, the tension applied at the time of winding is released and the band-shaped member 342*b* moves so as to be separated in the radial direction from the outer surface 115 of the catheter main body 110. When the band-shaped member 342*b* moves in the movement mode illustrated in FIG. 9B (first movement mode), the drug portion 130 is exposed to the living body tissue W by the covering state of the band-shaped member 342*b* being released.

Figure 10A:
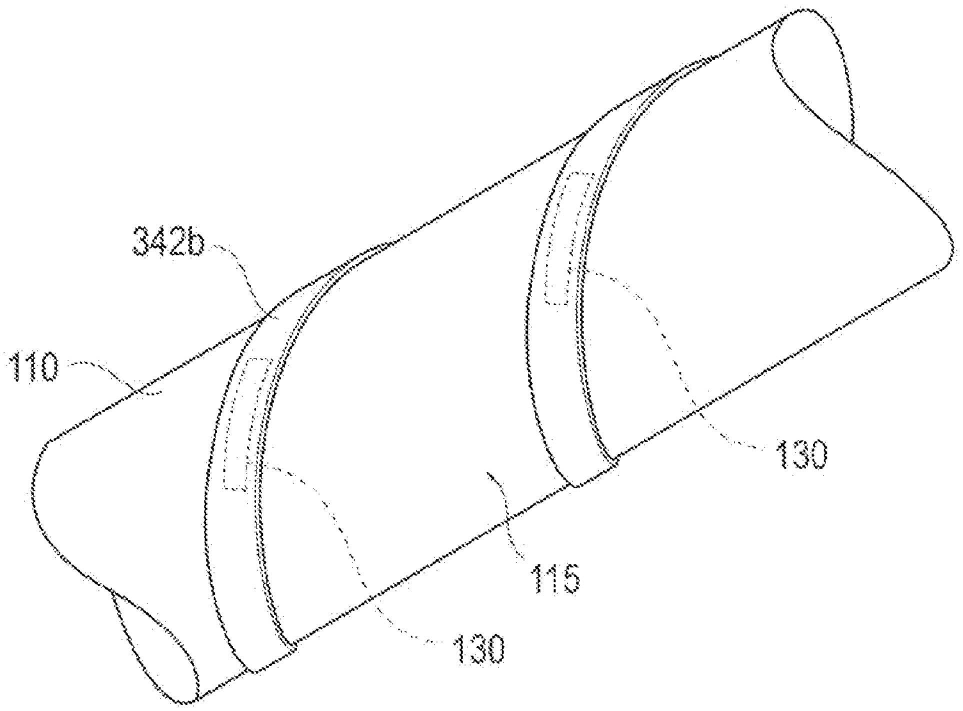
FIG. 10A is a schematic perspective view illustrating a state where the drug portion is covered with the band-shaped member of the introducer sheath according to the second embodiment.

As illustrated in FIG. 10A, the band-shaped member 342*b* is wound around the outer surface 115 of the catheter main body 110 so as to cover the disposition region 114 where the drug portion 130 is disposed in a state before the base portion 141 is rotated. In the state illustrated in FIG. 10A, the drug portion 130 is covered with the band-shaped member 342*b* as in the state illustrated in FIG. 9A, and thus the drug portion 130 does not come into contact with the living body tissue W and another member.

Figure 10B:
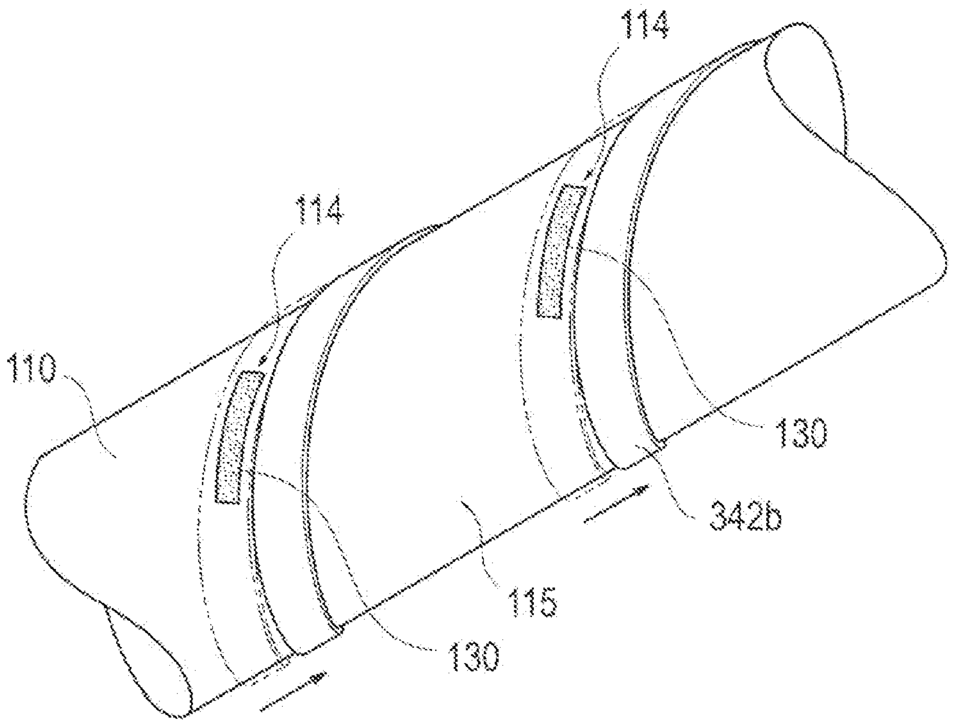
FIG. 10B is a schematic perspective view illustrating a state where the band-shaped member illustrated in FIG. 10A is moved in a second movement mode and the drug portion is exposed.

As illustrated in FIG. 10B, when the base portion 141 is rotated by an operator, the tension applied at the time of winding is released and the band-shaped member 342*b* moves in the axial direction of the catheter main body 110. When the band-shaped member 342*b* moves in the movement mode illustrated in FIG. 10B (second movement mode), the drug portion 130 is exposed to the living body tissue W by the covering state of the band-shaped member 342*b* being released. In FIG. 10B, the right side in the drawing is the proximal side of the catheter main body 110 and, by the tension being released, the band-shaped member 342*b* is loosened and released from the winding state and moves in the arrow direction illustrated in the drawing (to the proximal side).

Next, the movement modes of the band-shaped member 342*b* will be described. As illustrated in FIGS. 11B and 11C, in the introducer sheath 300 according to the second embodiment, the band-shaped member 342*b* has a substantially U-shaped cross section in the original state. In the event of tension application and stretching, the band-shaped member 342*b* is elastically deformed and the cross-sectional shape as illustrated in FIG. 11A becomes substantially linear (planar).

Figure 11A:
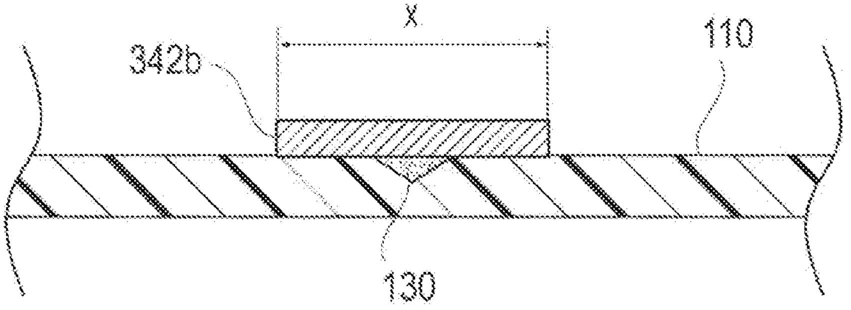
FIG. 11A is a conceptual diagram illustrating a state where the drug portion is covered with the band-shaped member of the introducer sheath according to the second embodiment.
Figure 11B:
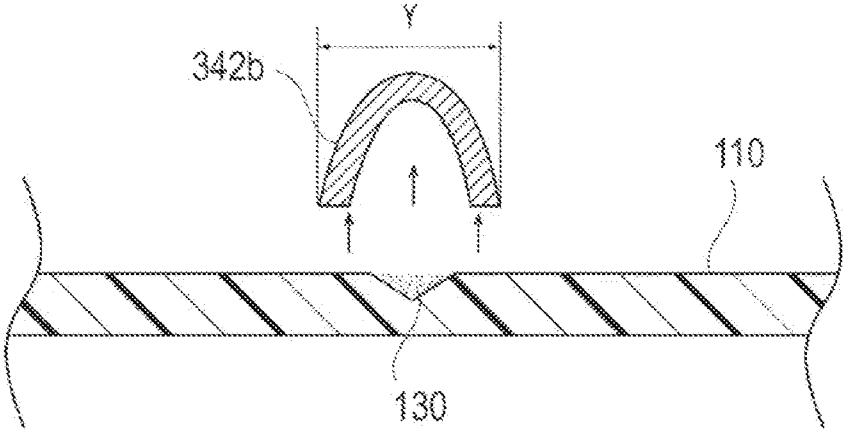
FIG. 11B is a conceptual diagram illustrating a deformation mode at the time when the tension of the band-shaped member illustrated in FIG. 11A is released.
Figure 11C:
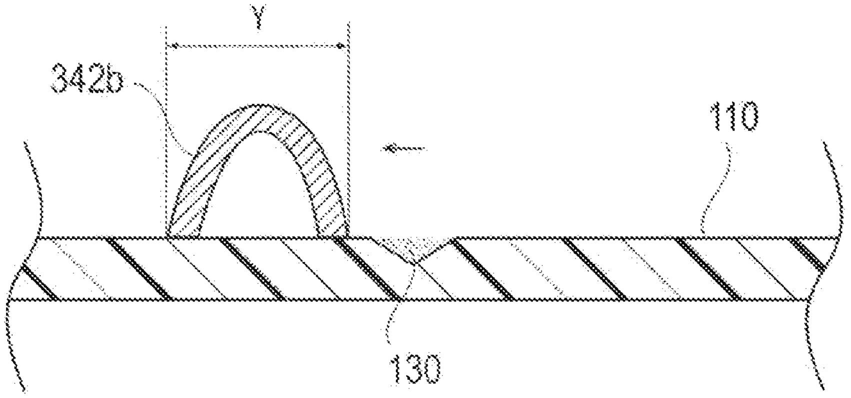
FIG. 11C is a conceptual diagram illustrating another deformation mode at the time when the tension of the band-shaped member illustrated in FIG. 11A is released.

As illustrated in FIG. 11A, the band-shaped member 342*b* is wound in a state where tension is applied to the outer surface 115 of the catheter main body 110 so as to cover the drug portion 130. When a predetermined tension is applied, the band-shaped member 342*b* is elastically deformed and stretched in the width direction and the axial direction, and the width dimension increases as compared with a state where no tension is applied. Here, X is the dimension of the tension-applied band-shaped member 342*b*.

As illustrated in FIG. 11B, when the base portion 141 is rotated with the tension applied, the tension applied to the band-shaped member 342*b* is gradually released with the rotational movement of the base portion 141. The band-shaped member 342*b* moves so as to be separated from the outer surface 115 of the catheter main body 110 as in the first movement mode illustrated in FIG. 9B to return to the original state. At this time, when the tension is released, the band-shaped member 342*b* decreases in width dimension to return to the original state by elastic deformation. Y is the dimension of the band-shaped member 342*b* at this time. As is apparent from comparison between FIGS. 11A and 11B, the band-shaped member 342*b* is restored to the original state by the tension being released, and thus the dimension Y is shorter than the dimension X.

As illustrated in FIG. 11C, when the base portion 141 is rotated with the tension applied, the tension applied to the band-shaped member 342*b* is gradually released with the rotational movement of the base portion 141. The band-shaped member 342*b* moves along the axial direction on the outer surface 115 of the catheter main body 110 as in the second movement mode illustrated in FIG. 10B to return to the original state. At this time, when the tension is released, the band-shaped member 342*b* decreases in width dimension to return to the original state by elastic deformation. Y is the dimension of the band-shaped member 342*b* at this time. As is apparent from comparison between FIGS. 11A and 11C, the band-shaped member 342*b* is restored to the original state by the tension being released, and thus the dimension Y is shorter than the dimension X.

As described above, by being configured by a stretchable elastic member, the band-shaped member 342*b* moves in a movement mode as illustrated in FIGS. 11B and 11C in which a restoration force acts as a result of elastic deformation. Accordingly, the band-shaped member 342*b* easily moves relative to the catheter main body 110.

It should be noted that although the band-shaped member 342*b* is capable of moving in at least one of the first movement mode and the second movement mode, the band-shaped member 342*b* is placed with pressure put by the living body tissue W, and thus it is easier for the band-shaped member 342*b* to move in the second movement mode than in the first movement mode. Of course, the band-shaped member 342*b* may move with the first movement mode and the second movement mode in combination with each other.

Figure 12A:
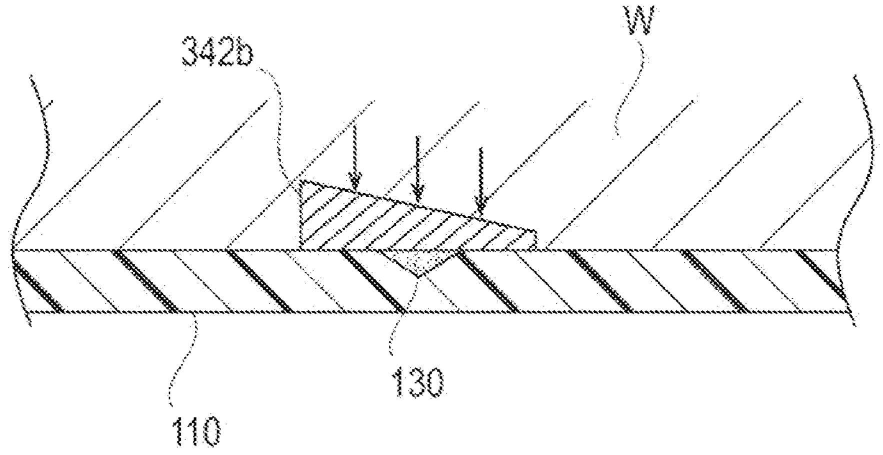
FIG. 12A is a conceptual diagram illustrating a state where the drug portion is covered with another example of the form of the band-shaped member of the introducer sheath according to the second embodiment.

In addition, in view of the mobility of the band-shaped member 342*b*, it is preferable that the band-shaped member 342*b* is formed such that the outer surface (upper surface) of the band-shaped member 342*b* is inclined toward the distal side of the catheter main body 110 with respect to the outer surface 115 of the catheter main body 110 as illustrated in FIG. 12A.

Figure 12B:
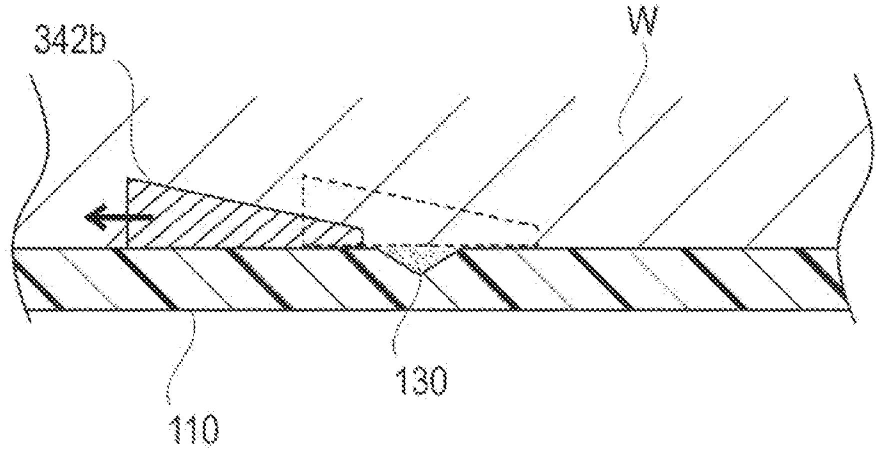
FIG. 12B is a conceptual diagram illustrating a movement mode at the time when the tension of the band-shaped member illustrated in FIG. 12A is released.

As illustrated in FIG. 12A, when the band-shaped member 342*b* is placed in the living body, the living body tissue W (for example, subcutaneous tissue) puts pressure on the band-shaped member 342*b* in the direction toward the axial center of the catheter main body 110 and, as illustrated in the drawing, the band-shaped member 342*b* is pressed in the direction toward the axial center of the catheter main body 110 (downward in the drawing). Accordingly, when the outer surface (upper surface) of the band-shaped member 342*b* is formed so as to be inclined toward the distal side of the catheter main body 110 with respect to the outer surface 115 of the catheter main body 110, as illustrated in FIG. 12B, the force toward the axial center of the catheter main body 110 applied to the upper surface of the band-shaped member 342*b* can be converted into a force toward the proximal side of the catheter main body 110. Accordingly, when the tension is released by the rotation operation of the base portion 141, the band-shaped member 342*b* easily moves to the proximal side of the catheter main body 110 along the outer surface 115 of the catheter main body 110 using the pressure force (pressing force) from the living body tissue W.

Next, an example of using the introducer sheath 300 will be described with reference to FIGS. 13A to 13D. As illustrated in FIG. 13A and so on, the region surrounded by the one-dot chain line corresponds to the puncture site P and the surrounding region.

As in the first embodiment, with the dilator 200 assembled in the introducer sheath 300, the catheter main body 110 of the introducer sheath 300 is inserted into the blood vessel V via the puncture site P formed in a patient's limb.

When the introducer sheath 300 is inserted into the blood vessel V, the mounting position of the distal member 342*a* of the band-shaped member 342*b* with respect to the catheter main body 110 remains fixed. Accordingly, when the introducer sheath 300 is inserted from the puncture site P, the band-shaped member 342*b* does not deviate from the catheter main body 110 due to the insertion resistance at the time of insertion into the puncture site P. The band-shaped member 342*b* is maintained in a state of covering the drug portion 130 so as not to come into contact with the living body tissue W or another member.

FIG. 13A is an enlarged view of the periphery of the support member of the introducer sheath that is placed in the living body lumen. As illustrated in FIG. 13A, the base portion 141 is not rotated, and thus the drug portion 130 is covered with the band-shaped member 342*b*. As illustrated in FIG. 13A, the base portion 141 is not rotated, and thus the drug portion 130 is covered with the covering member 142. Accordingly, the drug portion 130 is not eluted in the living body tissue W.

Figure 13B:
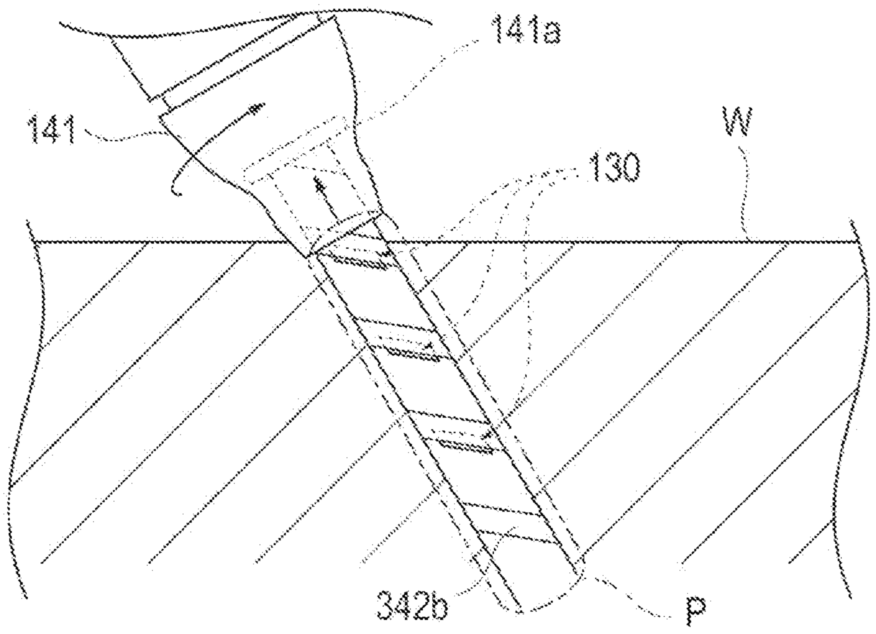
FIG. 13B is a conceptual diagram illustrating a state where the band-shaped member has begun to move by a rotation operation of a base portion.

An operator rotates the base portion 141 in a predetermined direction when a predetermined procedure is completed and an exposure timing of the drug portion 130 is reached. As illustrated in FIG. 13B, the tension applied to the band-shaped member 342*b* is released by this rotation operation. When the applied tension is released, the band-shaped member 342*b* is gradually loosened from the state of winding around the catheter main body 110 and begins to move along the axial direction of the catheter main body 110. As illustrated in FIG. 13B, the drug portion 130 begins to be gradually exposed in the living body tissue W as the band-shaped member 342*b* is moved by the rotation operation of the base portion 141. As illustrated in FIG. 13B, by the tension being released, the band-shaped member 342*b* is loosened and released from the winding state and moves to the proximal side of the catheter main body 110.

Figure 13C:
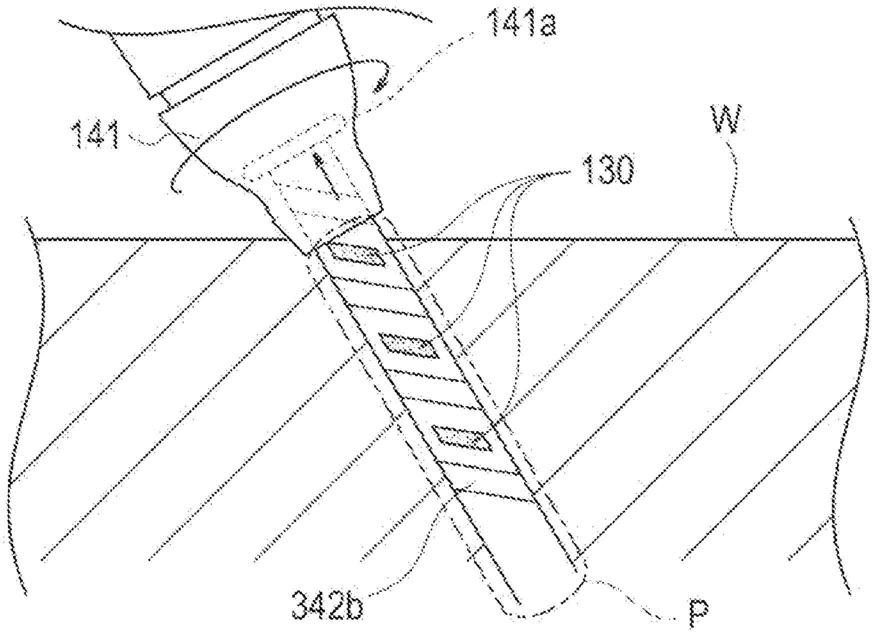
FIG. 13C is a conceptual diagram illustrating a state where the band-shaped member is moved by the rotation operation of the base portion and the drug portion is exposed.

As illustrated in FIG. 13C, the operator continues rotating the base portion 141 to expose the drug portion 130 covered with the band-shaped member 342*b* in the living body tissue W. In addition, until FIG. 13C is reached from FIG. 13B, the operator can adjust the amount of rotation of the base portion 141 to control the degree of the state of exposure of the drug portion 130. As a result, the operator can give an appropriate treatment to the puncture site P by the amount of elution of the drug 131 with respect to the living body tissue W being adjustable based on the degree of exposure of the drug portion 130 with respect to the living body tissue W.

Figure 13D:
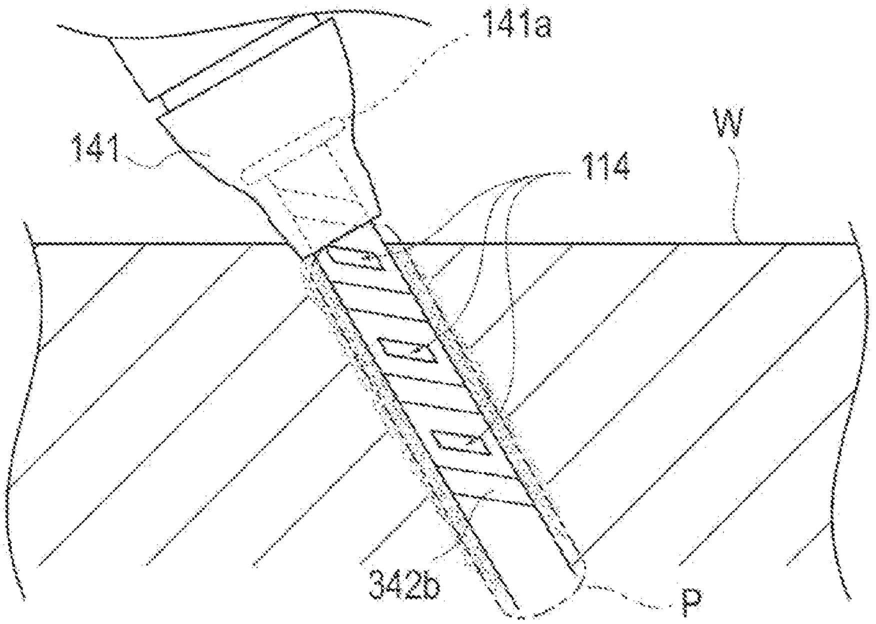
FIG. 13D is a conceptual diagram illustrating a state where the drug portion is exposed and absorbed around the puncture site.

Then, as illustrated in FIG. 13D, the drug 131 in the drug portion 130 exposed in the living body tissue W is eluted at the puncture site P and around the puncture site P. The drug 131 eluted in the living body tissue W is absorbed by the living body tissue W at the puncture site P and around the puncture site P to treat the wound and stop bleeding.

MODIFICATION EXAMPLE

Next, the modification example of the medical elongated body will be described with reference to FIGS. 14 and 15 as appropriate. This modification example is a modification example of the distal member 342*a* of the introducer sheath 300 according to the second embodiment. The introducer sheath 400 is configured such that the distal member 342*a* regulates the movement of the catheter main body 110 to the distal side at the time of, for example, insertion into the living body tissue W and the distal member 342*a* can be moved to the proximal side of the catheter main body 110 by the rotation operation of the base portion 141.

Figure 14A:
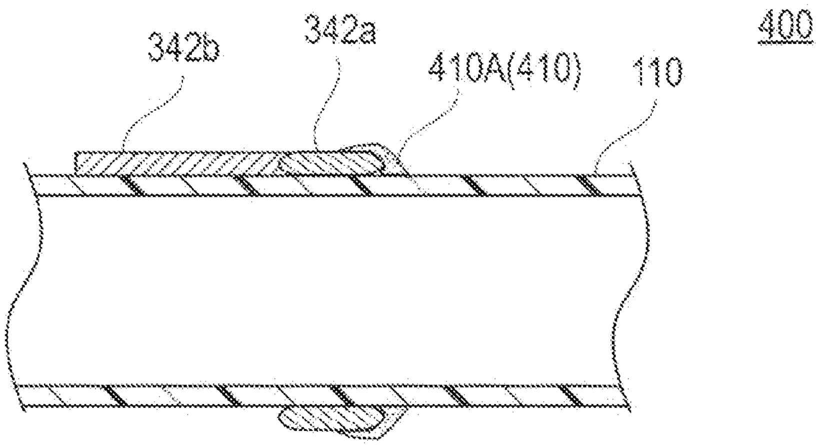
FIG. 14A is a conceptual diagram illustrating an example of the form of a distal member, which is a modification example of the introducer sheath according to the second embodiment.
Figure 14B:
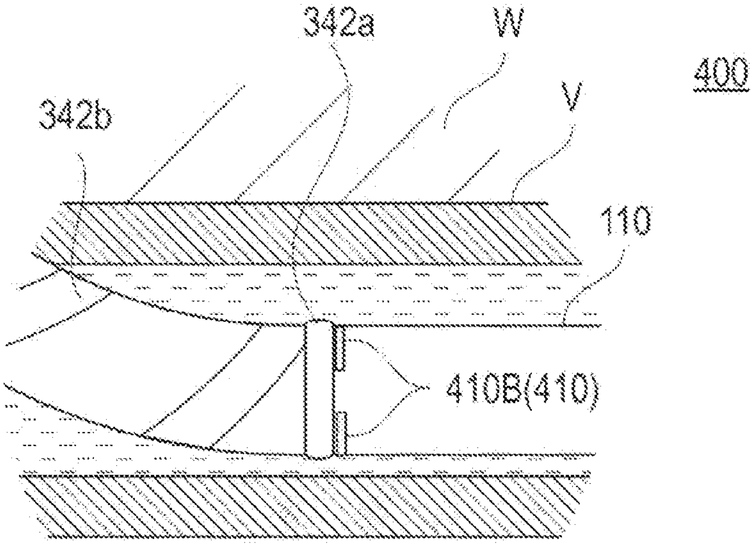
FIG. 14B is a conceptual diagram illustrating another example of the form of the distal member, which is a modification example of the introducer sheath illustrated in FIG. 14A.
Figure 15A:
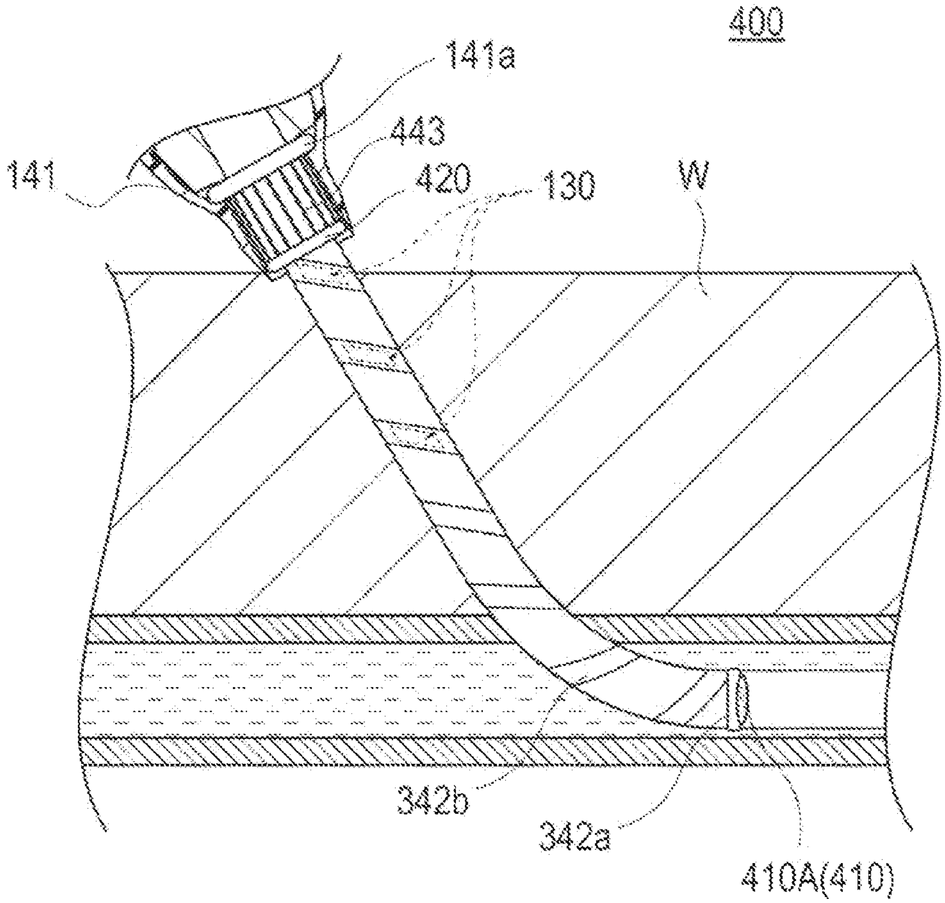
FIG. 15A is a conceptual diagram illustrating a state where the drug portion is covered before the distal member moves in the modification example of the introducer sheath according to the second embodiment.
Figure 15B:
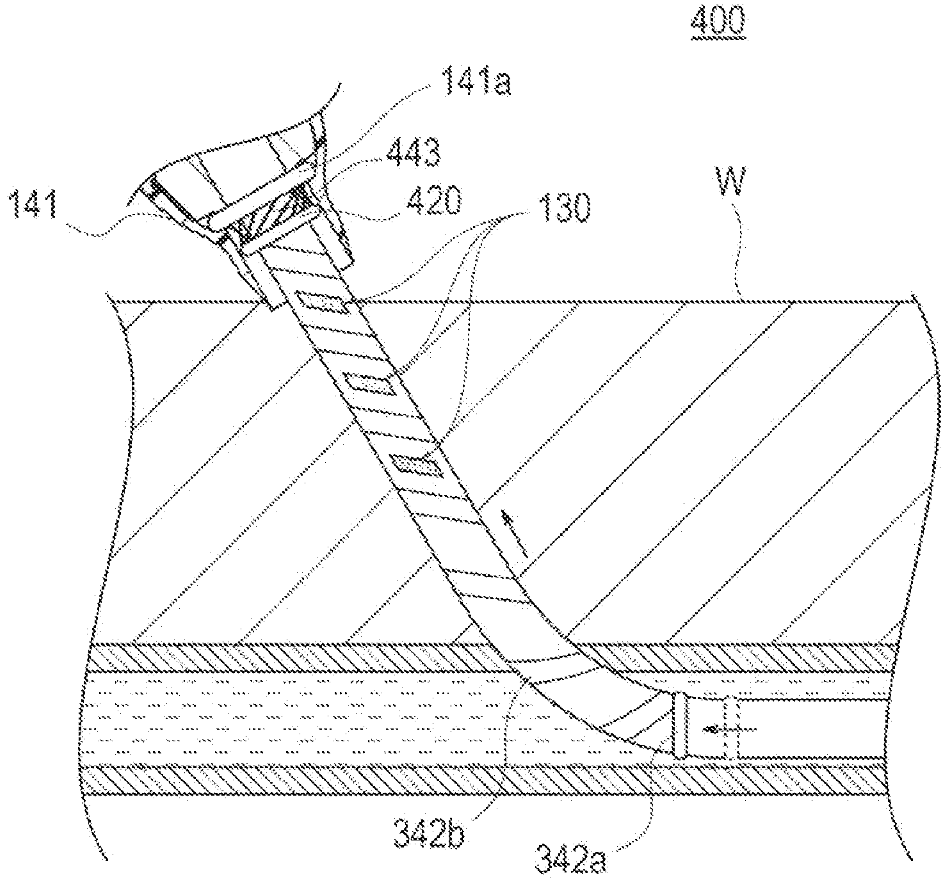
FIG. 15B is a conceptual diagram illustrating a state where the distal member is moved and the drug portion is exposed in the modification example of the introducer sheath according to the second embodiment.

FIGS. 14A and 14B illustrate an example of the form of the distal member 342*a* of the introducer sheath 400 according to the modification example. As illustrated in FIGS. 14A and 14B, the introducer sheath 400 is newly provided with a regulating portion 410 regulating the distal member 342*a* moving to the distal side with respect to the catheter main body 110. In addition, as illustrated in FIGS. 15A and 15B, the introducer sheath 400 is newly provided with a proximal member 420, the proximal end of the band-shaped member 342*b* is connected to the proximal member 420, and the proximal member 420 is provided so as to be movable with respect to the catheter main body 110. It should be noted that in FIGS. 14A and 14B, the distal side of the catheter main body 110 is the right side in the drawing.

The regulating portion 410 regulates the distal member 342*a* moving from the attachment position of the distal member 342*a* to at least the distal side of the catheter main body 110 with respect to the catheter main body 110. When the base portion 141 is rotated, the distal member 342*a* is capable of moving in the direction opposite to the direction of regulation by the regulating portion 410 (proximal end direction of the catheter main body 110). Accordingly, the band-shaped member 342*b* is capable of smoothly moving relative to the catheter main body 110.

FIG. 14A illustrates one form of the regulating portion 410. As illustrated in FIG. 14A, a regulating portion 410A is a part fixed to the catheter main body, specifically an adhesive layer provided such that the distal member 342*a* attached to the catheter main body 110 is temporarily fixed to the catheter main body 110 (temporary fixing state). As for the adhesive layer, the fixing state of the distal member 342*a* may be maintained at least until the base portion 141 is rotated (that is, until the drug portion 130 is exposed in the living body tissue W after the introducer sheath 300 is inserted into the living body). Since the distal member 342*a* is temporarily fixed by the adhesive layer that is the regulating portion 410, a movement relative to the catheter main body 110 is blocked or prevented, and yet the subsequent movement is not limited when the temporary fixing state is released. In other words, until the base portion 141 is rotated, the distal member 342*a* is in a state where at least a movement of the catheter main body 110 to the distal side is regulated.

When the state of temporary fixing by the adhesive layer is released with the movement direction of the distal member 342*a* regulated by the regulating portion 410A that is an adhesive layer, the distal member 342*a* is capable of moving relative to the catheter main body 110 in the directions to the distal and proximal sides. Accordingly, it is easier for the distal member 342*a* to move relative to the catheter main body 110 than in a state where the distal member 342*a* is fixed to the catheter main body 110.

An adhesive made of a biodegradable material such as collagen as an example can be used as an adhesive material that can be used for the adhesive layer. In addition, as for the adhesive layer, the limitation on the movement of the distal member 342*a* needs to be released at a predetermined timing (timing when the rotation operation of the base portion 141 is started). Accordingly, the adhesive layer is generated by appropriately adjusting, for example, the composition and mixing ratio of the biodegradable material that is used such that the temporary fixing of the distal member 342*a* is maintained for a predetermined time in view of, for example, the procedure time from the contact with the living body tissue W to the rotation operation of the base portion 141.

FIG. 14B illustrates another form of the regulating portion 410. As illustrated in FIG. 14B, a regulating portion 410B is configured by an engaging member engaging with at least a part of the distal member 342*a* attached to the catheter main body 110 and limiting a movement to the distal side with respect to the catheter main body 110. The engaging member is, for example, a protruding member provided on the outer surface 115 of the catheter main body 110 and blocks a movement from the attachment position of the distal member 342*a* to the distal side of the catheter main body 110 until the introducer sheath 400 is removed after insertion into the living body. It should be noted that the movement of the distal member 342*a* can be regulated more stably by a plurality of the regulating portions 410B being provided although at least one or more regulating portion 410B may be provided on the outer surface 115 of the catheter main body 110.

As described above, the regulating portion 410A illustrated in FIG. 14A and the regulating portion 410B illustrated in FIG. 14B regulate the movement of the distal member 342*a* by different methods. However, both are configured to regulate at least the movement of the distal member 342*a* to the distal side of the catheter main body 110.

The proximal member 420 is connected to the proximal end of the band-shaped member 342*b* and is connected to the ring member 141*a* via a connecting member 443. The connecting member 443 has the same function as the connecting member 143 illustrated in the first embodiment and may be configured by, for example, a linear member such as a wire. The proximal member 420 is provided so as to be movable along the axial direction with respect to the catheter main body 110. The connecting member 443 is wound up by the rotation of the ring member 141*a* rotating in conjunction with the rotation operation of the base portion 141, and the proximal member 420 moves to the proximal side of the catheter main body 110.

Next, an example of using the introducer sheath 400 of the modification example will be described. It should be noted that the distal member 342*a* will be described as a configuration provided with the regulating portion 410A configured by an adhesive layer made of a biodegradable material.

When the introducer sheath 400 is inserted from the puncture site P, the attachment position of the distal member 342*a* is temporarily fixed by the regulating portion 410A. Accordingly, no positional deviation of the distal member 342*a* occurs even when the catheter main body 110 is inserted in the living body. In addition, the drug portion 130 is covered with the band-shaped member 342*b* and is not eluted in the living body tissue W.

An operator rotates the base portion 141 in a predetermined direction when a predetermined procedure is completed and an exposure timing of the drug portion 130 is reached. In addition, at the timing when the rotation operation of the base portion 141 is started (that is, when the drug portion 130 is exposed), the adhesive layer that is the regulating portion 410 is biodegraded and the temporary fixing state of the distal member 342*a* is released. In other words, the distal member 342*a* becomes movable in the axial direction of the catheter main body 110.

As illustrated in FIG. 15B, when the base portion 141 is rotated, the introducer sheath 400 is deformed such that the connecting member 443 connected to the ring member 141*a* is wound up and the distance between the base portion 141 and the proximal member 420 decreases. As a result, as illustrated in FIG. 15B, the band-shaped member 342*b* begins to move relative to the catheter main body 110. By moving relative to the catheter main body 110 with the rotation of the base portion 141, the band-shaped member 342*b* exposes the drug portion 130 into the living body tissue W. The drug 131 in the drug portion 130 is eluted at the puncture site P and around the puncture site P and absorbed by the living body tissue W to stop bleeding at the wound.

[Action and Effect]

The medical elongated body according to the present embodiment described above includes: the catheter main body 110; the hub 120 fixed to the proximal portion of the catheter main body 110; the drug portion 130 disposed on the outer surface 115 of the catheter main body 110; and the support member 140 configured to be connected to the hub 120 and cover the drug portion 130 of the catheter main body 110. The support member 140 has the base portion 141 rotatable in the circumferential direction of the catheter main body 110 and the covering member 142 disposed so as to protrude from the distal end of the base portion 141 and cover the drug portion 130 while overlapping at least a part of the base portion 141 in the radial direction of the catheter main body 110. The covering member 142 is configured to move relative to the catheter main body 110 and expose the drug portion 130 as the base portion 141 rotates.

With such a configuration, an operator can expose the drug portion 130 covered with the covering member 142 in the living body tissue W by the simple operation of percutaneously inserting the catheter main body 110 into the blood vessel V from the puncture site P and rotating the base portion 141 in a predetermined direction with the covering member 142 inserted in the puncture site P. In addition, in the medical elongated body, the operation for exposing the drug portion 130 is only the rotation of the base portion 141, and thus the drug portion 130 can be quickly exposed in the living body tissue W. Accordingly, the operator can place the drug portion 130 at the puncture site P by a simple operation, and the time of hemostasis of the puncture site P can be shortened by the hemostatic action of the drug 131. In particular, in the case of using in combination with a hemostatic instrument for pressure hemostasis at the puncture site P, since the hemostasis time can be shortened by the drug 131, it is possible to reduce the risk of arterial occlusion or the like while reducing the operator's labor such as a decompression operation. Further, in the medical elongated body, when the drug portion 130 is exposed, the catheter main body 110 does not move from the state of being placed at the puncture site P, and thus there is no adverse effect such as twisting on the puncture site P or its surroundings. In addition, since the drug portion 130 is covered with the covering member 142 in a state where the base portion 141 is yet to be rotated, contact with the living body tissue W or another member can be prevented.

In addition, in the medical elongated body according to the present embodiment, preferably, the support member 140 may have the connecting member 143 connecting the base portion 141 and the covering member 142, and the connecting member 143 may be configured to be deformed such that the distance between the support member 140 and the covering member 142 in the axial direction of the catheter main body 110 decreases as the base portion 141 rotates.

As illustrated in, for example, FIGS. 2 and 15A, a linear member such as a wire that can be deformed such that the distance between the support member 140 and the covering member 142 decreases with the rotation of the base portion 141 can be used as the covering member 142. Since the support member 140 and the covering member 142 are connected by the connecting member 143 that can be deformed such that the distance decreases with the rotation of the base portion 141, an operator can smoothly rotate the base portion 141 with the catheter main body 110 inserted in the blood vessel V.

In addition, in the medical elongated body according to the present embodiment, preferably, the catheter main body 110 may have the first engaging portion in the outer surface 115, and the covering member 142 may have the second engaging portion configured to block rotation of the covering member 142 in the circumferential direction of the catheter main body 110 by engaging with the first engaging portion.

An operator rotates the base portion 141 in releasing the state of covering of the drug portion 130 with the covering member 142. At this time, since the first engaging portion and the second engaging portion are engaged with each other, rotation of the covering member 142 along the circumferential direction of the catheter main body 110 is blocked. Accordingly, the covering member 142 is not rotated together by the rotation operation of the base portion 141 or the like, and thus there is no adverse effect such as twisting on the puncture site P.

In addition, in the medical elongated body according to the present embodiment, preferably, the covering member 142 may have the main body portion 144 extending along the axial direction of the catheter main body 110 and the distal portion 145 extending from the main body portion 144 and positioned closer to the distal side than the drug portion 130 of the catheter main body 110, the first engaging portion may be the recessed groove portion 112 provided along the axial direction in the outer surface 115 of the catheter main body 110 and covered with the main body portion 144 in a state before the rotation of the base portion 141, and the second engaging portion may be the protruding protrusion portion 146 provided on the main body portion 144 and engaging with the groove portion 112.

In a state before the rotation operation of the base portion 141, the main body portion 144 of the covering member 142 covers the groove portion 112 provided in the outer surface 115 of the catheter main body 110. Accordingly, it is possible to suppress kink or buckling that is attributable to the groove portion 112 and may occur when the medical elongated body is inserted into a living body. In addition, since the first engaging portion and the second engaging portion are engaged with each other, the covering member 142 does not rotate along the circumferential direction of the catheter main body 110. Accordingly, the covering member 142 does not have an adverse effect such as twisting on the puncture site P.

In addition, in the medical elongated body according to the present embodiment, preferably, the distal portion 145 of the covering member 142 may have the tapered surface 145*a* inclined from the distal side of the main body portion 144 of the covering member 142 toward the outer surface 115 of the catheter main body 110.

Since the distal portion 145 is inclined from the distal side of the main body portion 144 toward the outer surface 115 of the catheter main body 110, the insertion resistance at the time of inserting the medical elongated body into a living body is reduced. As a result, an operator can smoothly insert the medical elongated body from the puncture site P.

In addition, in the medical elongated body according to the present embodiment, preferably, the catheter main body 110 may have the recess portion 113 positioned closer to the distal side than the drug portion 130, and the distal end 145*b* of the distal portion 145 may be configured to fit into the recess portion 113 in the state before the rotation of the base portion 141.

In a state where the base portion 141 is yet to be rotated, the covering member 142 is in a state where the distal end 145*b* of the distal portion 145 is fitted with the recess portion 113. Accordingly, the clearance between the catheter main body 110 and the distal end 145*b* of the distal portion 145 is infinitely equal to zero. Accordingly, the medical elongated body is reduced in insertion resistance at the time of insertion into a living body. As a result, an operator can smoothly insert the medical elongated body from the puncture site P.

In addition, in the medical elongated body according to the present embodiment, preferably, the covering member 342 may be configured to have: the distal member 342*a* disposed closer to the distal side than the drug portion 130 of the catheter main body 110; and the band-shaped member 342*b* disposed by connecting the distal member 342*a* and the base portion 141 in a state of covering the drug portion 130 of the catheter main body 110 in a state before the rotation of the base portion 141.

Since the covering member 342 is positioned closer to the distal side than the drug portion 130, an operator can easily grasp the distal end position of the drug portion 130. In addition, by rotating the base portion 141 in a predetermined direction with the covering member 142 placed at the puncture site P, an operator can move the band-shaped member 342*b* relative to the catheter main body 110 and expose the drug portion 130 in the living body tissue W.

In addition, in the medical elongated body according to the present embodiment, preferably, the distal member 342*a* may be configured to be fixed to the catheter main body 110 at a position closer to the distal side than the drug portion 130 of the catheter main body 110.

With such a configuration, the distal member 342*a* connected to the distal end of the band-shaped member 342*b* does not deviate from the attachment position with respect to the catheter main body 110 due to the insertion resistance at the time when the medical elongated body is inserted into the puncture site P. Accordingly, the state of covering of the drug portion 130 with the band-shaped member 342*b* is maintained in a state before the rotation operation of the base portion 141. As a result, contact of the drug portion 130 with the living body tissue W or another member is prevented until the base portion 141 is rotated.

In addition, in the medical elongated body according to the present embodiment, preferably, the distal member 342*a* may be configured to have the regulating portion 410 regulating a movement in the distal end direction with respect to the catheter main body 110.

With such a configuration, the regulating portion 410 regulates the distal member 342*a* moving to the distal side of the catheter main body 110. Accordingly, when the medical elongated body is inserted into the puncture site P, the distal member 342*a* does not move due to the insertion resistance. Accordingly, the state of covering of the drug portion 130 with the band-shaped member 342*b* is maintained such that the drug portion 130 does not come into contact with the living body tissue W or another member in a state before the rotation operation of the base portion 141. In addition, since the distal member 342*a* is capable of moving in the direction opposite to the direction of regulation by the regulating portion 410 when the base portion 141 is rotated, the band-shaped member 342*b* can be smoothly moved relative to the catheter main body 110.

In addition, in the medical elongated body according to the present embodiment, preferably, the band-shaped member 342*b* may be configured by an elastic member, and the band-shaped member 342*b* may be configured to be wound around the catheter main body 110 in a state where a predetermined tension is applied and deformed such that the width dimension decreases when the tension is released by the rotation of the base portion 141.

The band-shaped member 342*b* is wound around the catheter main body 110 in a state of being stretched and widened with tension applied. When the tension is released with the rotational movement of the base portion 141, the band-shaped member 342*b* is to return to the original state by elastic deformation. As illustrated in FIGS. 9B and 10B, the band-shaped member 342*b* at this time is in a movement mode in which a restoration force attributable to elastic deformation acts to decrease the width dimension and thus is relatively easy to move with respect to the catheter main body 110. Accordingly, the state of covering of the drug portion 130 with the band-shaped member 342*b* is likely to be released simply by the rotation operation of the base portion 141.

In addition, in the medical elongated body according to the present embodiment, preferably, the outer surface 115 of the band-shaped member 342*b* may be inclined toward the distal side of the catheter main body 110.

Since the outer surface 115 of the band-shaped member 342*b* is inclined toward the distal side of the catheter main body 110, the force toward the axial center of the catheter main body 110 that is applied to the outer surface (upper surface) of the band-shaped member 342*b* (such as the pressure force of the living body tissue W) can be converted into a force toward the proximal side of the catheter main body 110. Accordingly, when the tension is released by the rotation operation of the base portion 141, the band-shaped member 342*b* easily moves to the proximal side of the catheter main body 110 along the outer surface 115 of the catheter main body 110 using the pressure force (pressing force) from the living body tissue W.

The detailed description above describes embodiments of a medical elongated body and operational method representing examples of the new medical elongated body and operational method disclosed here. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents that fall within the scope of the claims are embraced by the claims.

What is claimed is:

1. A medical elongated body comprising:

a catheter main body possessing an outer surface and a proximal portion;

a hub fixed to the proximal portion of the catheter main body;

a drug disposed on the outer surface of the catheter main body;

a support member connected to the hub and covering the drug disposed on the outer surface of the catheter main body;

the support member including a base portion rotatable in a circumferential direction of the catheter main body and a covering member that protrudes distally beyond a distal end of the base portion, the covering member covering the drug disposed on the outer surface of the catheter main body and overlapping at least a part of the base portion in a radial direction of the catheter main body, the base portion encircling a portion of the hub; and the covering member being movable relative to the catheter main body and being connected to the base portion so that rotation of the base portion moves the covering member to expose the drug portion and results in a portion of the support member other than the base portion being spiral-shaped after exposure of the drug portion.

2. The medical elongated body according to claim 1, wherein the portion of the support member that is spiral-shaped after exposure of the drug portion is a connecting member connecting the base portion and the covering member so that the rotation of the base member results in the movement of the covering member relative to the catheter main body, and the connecting member is deformable into the spiral-shape such that a distance between the base portion and the covering member in an axial direction of the catheter main body decreases as the base portion rotates.

3. The medical elongated body according to claim 1, wherein the catheter main body has a first engaging portion in the outer surface, and the covering member has a second engaging portion that is in engagement with the first engaging portion to block rotation of the covering member in the circumferential direction of the catheter main body.

4. The medical elongated body according to claim 3, wherein the covering member includes a main body portion extending along an axial direction of the catheter main body and a distal portion extending distally from the main body portion and distally beyond a distal end of the drug disposed on the outer surface of the catheter main body, the first engaging portion is an axially extending recessed groove in the outer surface of the catheter main body, the main body portion covering the groove before the rotation of the base portion and being moved to a position in which the groove is exposed after the rotation of the base portion, and the second engaging portion is a protrusion provided on the main body portion and engaging with the groove.

5. The medical elongated body according to claim 4, wherein the distal portion of the covering member has a tapered surface inclined from a distal side of the main body portion of the covering member toward the outer surface of the catheter main body.

6. The medical elongated body according to claim 4, wherein the catheter main body includes a recess positioned distal of a distal end of the drug, and a distal end of the distal portion of the covering member is positioned in the recess before the rotation of the base portion.

7. The medical elongated body according to claim 1, wherein the covering member includes:

a distal member disposed distal of a distal end of the drug on the outer surface of the catheter main body; and a band-shaped member connected to both the distal member and the base portion while covering the drug on the outer surface of the catheter main body before the rotation of the base portion, the band-shaped member being the portion of the support member that is spiral-shaped after exposure of the drug portion.

8. The medical elongated body according to claim 7, wherein the distal member is fixed to the catheter main body at a position distal of a distal end of the drug on the outer surface of the catheter main body.

9. The medical elongated body according to claim 7, further comprising a regulating portion regulating movement of the distal member in a distal end direction with respect to the catheter main body, the regulating portion being a part fixed to the catheter main body and contacting the distal member.

10. The medical elongated body according to claim 7, wherein the band-shaped member is an elastic member, and the band-shaped member is wound around the catheter main body in a state where a predetermined tension is applied to the band-shaped member and the band-shaped member is deformed such that a width dimension of the band-shaped member decreases when the tension is released by the rotation of the base portion.

11. The medical elongated body according to claim 7, wherein an outer surface of the band-shaped member is inclined toward a distal side of the catheter main body.

12. A medical elongated body comprising:

a catheter main body possessing a distal end and proximal portion terminating at a proximal end, the catheter main body including a lumen that is open at opposite ends and that extends in an axial direction of the catheter main body from the distal end of the catheter main body to the proximal end of the catheter main body, the catheter main body possessing an outer surface;

a hub fixed to the proximal portion of the catheter main body;

a drug that contains a hemostatic agent to treat a wound site in a living body, the drug being located on an axially extending drug covered region on the outer surface of the catheter main body;

a base that is tubular and includes a proximal end and a distal end, the base being rotatably connected to the hub and being rotatable relative to the catheter main body;

a cover that includes a distal portion extending distally beyond the distal end of the base, the cover extending axially over a longitudinal extent that axially overlaps with at least a distal portion of the drug covered region on the outer surface of the catheter main body at which the drug is located so that the distal portion of the drug covered region on the outer surface of the catheter main body at which the drug is located is covered by the distal portion of the cover;

the proximal portion of the cover being operatively connected to the base by a connecting member that deforms when the base is rotated so that cover moves toward the hub; and the cover including a proximal portion operatively connected to the base so that the rotation of the base results in movement of the distal portion of the cover that uncovers and exposes the drug in the distal portion of the drug covered region.

13. The medical elongated body according to claim 12, wherein the connecting member is a wire.

14. The medical elongated body according to claim 12, further comprising an axially extending groove and a protrusion positioned in the groove, one of the groove and the protrusion being provided on the catheter main body, and the other of the protrusion and the groove being provided on the cover, the positioning of the protrusion in the groove preventing the cover from rotating when the base is rotated.

15. The medical elongated body according to claim 12, further comprising a recess formed in the outer surface of the catheter main body at a location distal of the drug covered region on the outer surface of the catheter main body, the cover including a part at the distal portion of the cover that is positioned in the recess.

16. The medical elongated body according to claim 12, wherein the cover is a band that extends helically about the catheter main body, with axially spaced-apart adjacent windings.

17. The medical elongated body according to claim 16, wherein the band that extends helically about the catheter main body possesses a distal end connected to a distal member, the distal member being fixed to the catheter main body at a position distal of the drug covered region.

18. The medical elongated body according to claim 17, wherein the distal member is temporarily fixed to the catheter main body so that the distal member becomes movable relative to the catheter main body when the base is rotated.

19. A medical elongated body comprising:

a catheter main body extending in a longitudinal direction and possessing an outer surface and a proximal portion;

a hub fixed to the proximal portion of the catheter main body;

a drug disposed on the outer surface of the catheter main body;

a support member connected to the hub and covering the drug disposed on the outer surface of the catheter main body;

the support member including a base portion encircling a portion of the hub and rotatable relative to the catheter main body in a circumferential direction of the catheter main body, the support member also including a covering member having a distal portion that protrudes distally beyond a distal end of the base portion, the covering member covering the drug disposed on the outer surface of the catheter main body and overlapping at least a part of the base portion in a radial direction of the catheter main body;

a groove that extends in the longitudinal direction and a protrusion positioned in the groove and movable along the groove, the groove being provided on one of the catheter main body and the cover member while the protrusion is provided on an other one of the catheter main body and the cover member; and the protrusion and the groove being configured so that: i) the protrusion positioned in the groove prevents rotation of the cover relative to the catheter main body when the base portion is rotated; and ii) the protrusion moves along the groove in the longitudinal direction when the base portion is rotated to move the covering member along the catheter main body to expose the drug portion.

20. The medical elongated body according to claim 19, wherein the drug is located in a disposition region of the catheter main body and the drug terminates at a distal end of the disposition region, the catheter main body including a recess on a distal side of the distal end of the disposition region, a part of the covering member at the distal portion of the covering member being positioned in the recess before the rotation of the base portion.

* * * * *